US010094825B2

(12) United States Patent
Mesa et al.

(10) Patent No.: US 10,094,825 B2
(45) Date of Patent: Oct. 9, 2018

(54) PREDICTIVE BIOMARKERS FOR DETECTION OF ORGAN DAMAGE IN AUTOIMMUNE ILLNESSES AND OTHER DISEASES

(71) Applicants: Annia Mesa, Miami, FL (US); Jason A. Somarelli, Durham, NC (US)

(72) Inventors: Annia Mesa, Miami, FL (US); Jason A. Somarelli, Durham, NC (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/225,395

(22) Filed: Aug. 1, 2016

(65) Prior Publication Data

US 2017/0030906 A1    Feb. 2, 2017

Related U.S. Application Data

(60) Provisional application No. 62/199,118, filed on Jul. 30, 2015.

(51) Int. Cl.
G01N 33/00 (2006.01)
G01N 33/564 (2006.01)
G01N 33/68 (2006.01)

(52) U.S. Cl.
CPC ....... *G01N 33/564* (2013.01); *G01N 33/6854* (2013.01); *G01N 2800/104* (2013.01); *G01N 2800/50* (2013.01)

(58) Field of Classification Search
CPC .................. G01N 33/564; G01N 33/6854
See application file for complete search history.

(56) References Cited

PUBLICATIONS

UniProtKB—P09012 (SNRPA_Human). Nov. 1, 1988. v3 (attached) Jan. 23, 2007. 282 amino acids. (Year: 2007).*
Poole et al., (Arth Rheum. Mar. 2009;60(3):848-859). (Year: 2009).*
Allen, D. et al., "Evaluating systemic lupus erythematosus patients for lung involvement," *Lupus*, 2012, Abstract only.
(Continued)

*Primary Examiner* — Cherie M Stanfield
(74) *Attorney, Agent, or Firm* — Saliwanchik, Lloyd & Eisenschenk

(57) ABSTRACT

The invention provides methods for identifying the presence of, or an increased risk of developing, organ damage in a subject having an autoimmune disease, for example, Systemic Lupus Erythematosus (SLE) or Mixed Connective Tissue Disease (MCTD), or other disease in which the lungs and/or kidneys are involved. In one embodiment, a significantly increased combined IgM reactivity against the peptides having the sequences of SEQ ID NOs: 4, 9, 12, and 15 in a sample obtained from a patient compared to a healthy control indicates lung damage or an increased risk of developing lung damage in the subject. In another embodiment, a significantly increased combined IgM reactivity against the peptides having the sequences of SEQ ID NOs: 2, 8, 12, 14, 15, and 17, in a sample from a patient compared to a healthy control indicates kidney damage or an increased risk of developing kidney damage in the subject.

19 Claims, 4 Drawing Sheets

Specification includes a Sequence Listing.

(56) References Cited

PUBLICATIONS

Amigues, J.M. et al., Comparative study of 4 diagnosis criteria sets for MCTD in patients with anti-RNP antibodies (1996). Autoimmunity group of the hospital of Toulouse. J Rheumatol. 12:2055-2062—Abstract only.

Arbuckle, M.R. et al., "A limited lupus anti-spliceosomal response targets a cross-reactive, proline-rich motif," *J Autoimmun*, 1998, 11:431-438.

Barakat, S. et al., "Mapping of epitopes on U1 snRNP peptide A with synthetic peptides and autoimmune sera," 1991, *Clin Exp Immunol.*, 86:71-78.

Bertoli, A.M. et al., "Systemic lupus erythematosus in a multiethnic US Cohort Lumina XLVIII: factors predictive of pulmonary damage," Lupus, 2007, Abstract only.

Braun-Moscovici, Y. et al., Rituximab: rescue therapy in life-threatening complications or refractory autoimmune diseases: a single center experience. *Rheumatol Int.*, 2013, Abstract only.

Brugos, B. et al., "Serum and urinary cytokine levels of SLE patients," *Pharmazie*, 2012, 67:411-413.

Casciola-Rosen, L. et al., "Cleavage by granzyme B is strongly predictive of autoantigen status: implications for initiation of autoimmunity," *J Exp Med*, 1999 190:815-26.

Chen, Y-Ig et al., "Proteomic analysis of in vivo-assembled pre-mRNA splicing complexes expands the catalog of participating factors," *Nucleic Acids Res*, 2007, 35:3928-3944.

Cojocaru, M. et al., "Pulmonary manifestations of systemic autoimmune diseases," *Maedica*, 2011, 6:224-229.

De Clerck, L.S. et al., "Is MCTD a distinct entity? Comparison of clinical and laboratory findings in MCTD, SLE, PSS, and RA patients," *Clin Rheumatol*, 1989, 8:29-36—Abstract only.

De Wildt R.M., "Isolation and characterization of single anti-U1A-specific B cells from autoimmune patients," *Ann N Y Acad Sci.*, 1997, 815:440-442.

Faig, O.Z., et al., "Novel specificity of anti-U1A autoimmune patient sera," *Scand J Immunol.*, 2003, 57:79-84.

Gutsche, M. et al., Connective Tissue Disease-associated Interstitial Lung Disease: A review, *Curr Respir Care Rep.*, 2012, 21:224-232.

Haase, M. et al., "Accuracy of neutrophil gelatinase-associated lipocalin (NGAL) in diagnosis and prognosis in acute kidney injury: a systematic review and meta-analysis," *Am J Kidney Dis.*, 2009, 54:1012-1024.

Hochberg, M.C., "Updating the America College of Rheumatology revised criteria for the classification of systemic lupus erythematosus." *Arthritis Rheum.*, 1997, 40:1725.

Jessen, T.H. et al., "Identification of molecular contacts between the U1A small nuclear ribonucleoprotein and U1 snRNA," *The EMBO J.*, 1991, 10:3447-3456.

Jin, L. et al., "Peripheral CD24(hi) CD27(+) CD19(+) B cells subset as a potential biomarker in naïve systemic lupus erythematosus," *Int J Rheum Dis.*, 2013, 16:698-708—Abstract only.

Lage, L.V. et al., "Fluctuation of anti-endothelial cell antibody titers in mixed connective tissue disease," *Isr Med Assoc J.*, 2012, 14:84-87.

Levitt, J.E. et al., "Early acute lung injury: criteria for identifying lung injury prior to the need for positive pressure ventilation," *Crit Care Med.*, 2013, 41:1929-1937.

Lu J. et al., "An RBD that does not bind RNA: NMR secondary structure determination and biochemical properties of the C-terminal RNA binding domain from the human U1A protein," *J Mol Biol.*, 1995, 247:739-752—Abstract only.

Luyckx, A. et al., "Clinical relevance of measurement of antibodies to individual snU1-RNP proteins," *Clin Chem*, 2005, 51:1888-1890.

Maldonado, M.E. et al., "Clinical and immunologic manifestations of mixed connective tissue disease in a Miami population compared to a Midwestern US Caucasian population," *J Rheumatol.*, 2008, 35:429-437.

McClain, M.T. et al., "Structural availability influences the capacity of auto-antigenic epitopes to induce a widespread lupus-like autoimmune respons," *Proc Natl Acad Sci.*, 2004, 101:3551-3556.

Mesa, A. et al., "Differential immunoglobulin class-mediated responses to components of the U1 small nuclear ribonucleoprotein particle in systemic lupus erythematosus and mixed connective tissue disease," *Lupus*, 2013, 22:1371-1381.

Mevorach, D. et al., "Systemic lupus erythematosus and apoptosis: a question of balance," *Clin Rev Allergy Immunol.*, 2003, 25:49-60—Abstract only.

Migliorini, P. et al., "Anti-Sm and anti-RNP antibodies," *Autoimmunity*, 2005, 38:47-54—Abstract only.

Moore, M.J. et al. "Evidence for two active sites in the splicesome provided by stereochemistry of pre-mRNA," *Nature*, 1993, 23:364-368.

Muñoz-Paredes, J.C. et al., "Development and standardization of an indirect ELISA for the serological diagnosis of classical swine fever," *Pesq Vet Bra*, 1999, 19:123-127.

Nishimaki, T. et al., "Immunological analysis of pulmonary hypertension in connective tissue diseases," *J Rheumatol.*, 1999, Abstract only.

Nowicka-Sauer, K. et al., "Neuropsychological assessment in mixed connective tissue disease: Comparison with systemic lupus erythematosus," *Lupus*, 2012, Abstract only.

Pehlivan, O. et al., "Pulmonary arterial hypertension related to connective tissue diseases," *Anadolu Kardiyol Derg.*, 2010, 1:57-62.

Perkins, K. et al., "A Rasch analysis for classification of systemic lupus erythematosus and mixed connective tissue disease," *J Appl Meas.*, 2008, 9:136-50.

Pizarro, S. et al., "Soluble vascular cell adhesion molecule-1 indicates SLE disease activity and specific organ involvement," *Rev Alerg Mex.*, 2007, 54:189-95.

Poole, B.D. et al., "Early targets of nuclear RNP humoral autoimmunity in human systemic lupus erythematosus," *Arthritis Rheum*, 2009, 60:848-859.

Rebora, A. et al., "Mixed connective tissue disease and correlated diseases," *G Ital Dermatol Venereol.*, 1990, Abstract only.

Roy, A., et al., "COFACTOR: an accurate comparative algorithm for structure-based protein function annotation," *Nucleic Acids Res.*, 2012 (Web Server issue): W471-7.

Roy, A. et al., "I-TASSER: a unified platform for automated protein structure and function prediction," *Nat Protoc.*, 2010, 5:725-738.

Sasaki, N., "A histopathological study of pulmonary hypertension in connective tissue disease," *Allergol Int.*, 2011, 60:411-417.

Sato, T. et al., "Anti-U1 RNP antibodies in cerebrospinal fluid are associated with central neuropsychiatric manifestations in systemic lupus erythematosus and mixed connective tissue disease," *Arthritis Rheum.*, 2010, 62:3730-3740.

Sawai, T. et al., "Morphometric analysis of the kidney lesions in mixed connective tissue disease (MCTD)," *Tohoku J Exp Med.*, 1994, 174:141-154.

Scherly D. et al., "Identification of the RNA binding segment of human U1A protein and definition of its binding site on U1 snRNA," *The EMBO J,*, 1989, 8:4163-4170.

Sharp, G.C. et al., "Mixed connective tissue disease—an apparently distinct rheumatic disease syndrome associated with a specific antibody to an extractable nuclear antigen (ENA)," *Am J Med*, 1972, 52:148-159—Abstract only.

Simón, J.A. et al., "Anti-nucleosome antibodies in patients with systemic lupus erythematosus of recent onset. Potential utility as a diagnostic tool and disease activity marker," *Rheumatology*, 2004, 43:220-224.

Somarelli, J.A. et al., "Epitope mapping of the U1 small nuclear ribonucleoprotein particle in patients with systemic lupus erythematosus and mixed connective tissue disease," Lupus, 2011, 20:274-289.

Somarelli, J.A. et al., "Genome-based identification of spliceosomal proteins in the silk moth *Bombyx mori,*" *Arch of Insect Biochem and Physiol.*, 2010, 75:231-263.

Swanton, J. et al., "Mixed connective tissue disease: Still crazy after all these years," *Rheum Dis Clin North Am*, 2005, 31:421-436—Abstract only.

(56) References Cited

OTHER PUBLICATIONS

Talken, B.L. et al.,"T cell epitope mapping of the Smith antigen reveals that highly conserved Smith antigen motifs are the dominant target of T cell immunity in systemic lupus erythematosus," *J Immunol.*, 2001, 167:562-568.

Tang, J. et al., "Characterization of yeast U1 snRNP A protein: identification of the N-terminal RNA binding domain (RBD) binding site and evidence that the C-terminal RBD functions in splicing," *RNA*, 1996, 10:1058-1070.

Varani, L. et al., "The NMR structure of the 38 kDa U1A protein—PIE RNA complex reveals the basis of cooperativity in regulation of polyadenylation by human U1A protein," *Nat Struct Biol.*, 2000, 7:329-335—Abstract only.

Vlachoyiannopoulos, P.G. et al., "Predominance of IgM anti-U1RNP antibodies in patients with systemic lupus erythematosus," *Br J Rheumatol.*, 1996, 35:534-541.

Watanabe, Y. et al., "Rapidly progressive respiratory failure in mixed connective tissue disease: report of an autopsy case," Intern Med., 2012, 5:3415-3419.

Yang, C.C. et al., "Urinary neutrophil gelatinase-associated lipocalin is a potential biomarker for renal damage in patients with systemic lupus erythematosus," *J Biomed Biotechnol.*, 2012, 2012:759313.

Yoshida, A. et al., "Nephropathy in patients with mixed connective tissue disease," Ryumachi., 1994, 34(6):976-980—Abstract only.

Zhang, Y., "I-TASSER server for protein 3D structure prediction," *BMC Bioinformatics*, 2008, 9:40.

Zhang, L. et al., "Discovery and identification of anti-U1-A anRNP antibody in lung cancer," *Sci China C Life Sci.*, 2005, 48:641-647—Abstract only.

\* cited by examiner

PREDICTIVE BIOMARKERS FOR DETECTION OF ORGAN DAMAGE IN AUTOIMMUNE ILLNESSES AND OTHER DISEASES

CROSS REFERENCE TO RELATED APPLICATION(S)

This application claims the benefit of U.S. Provisional Application Ser. No. 62/199,118, filed Jul. 30, 2015, which is hereby incorporated by reference in its entirety, including any figures, tables, or drawings.

GOVERNMENT SUPPORT

This invention was made with government support under GM061347, AR048805, and GM008205 awarded by the National Institutes of Health. The government has certain rights in the invention.

The Sequence Listing for this application is labeled "SeqList-25Jul16.txt", which was created on Jul. 25, 2016, and is 5 KB. The entire content is incorporated herein by reference in its entirety.

BACKGROUND OF INVENTION

Autoimmune diseases develop when the immune system misidentifies a self-antigen as a foreign antigen and produces destructive responses to the self-antigen.

Patients with autoimmune disease frequently develop kidney involvement and/or lung malfunction. Identification of the potential for such organ involvement is clinically important so that these patients can be treated differently.

Systemic Lupus Erythematosus (SLE) and Mixed Connective Tissue Disease (MCTD) are chronic autoimmune diseases that target overlapping auto-antigens and exhibit similar clinical manifestations.

Previous studies have confirmed that components of the U1 small nuclear ribonucleoprotein complex (snRNP) such as U1A are 1000-fold more autoantigenic than any other nuclear component in SLE patients. The small nuclear RNP A (referred to here as "U1Ap"), in combination with U1-70K and U1C, is a specific U1 RNP peptide that, along with the U1-RNA and Smith (Sm) proteins, forms an active U1 snRNP complex. This complex, in turn, plays an essential role in pre-mRNA processing as a functional unit of the spliceosome. The U1Ap is composed of two RNA recognition motifs (RRM) located at the N- and C-tellninal of this spliceosomal protein and has been reported to be conserved across the eukaryote domain.

The N-terminal RRM domain 1 (RRM1) of U1Ap has been extensively studied and has been shown to be necessary and sufficient to bind U1-RNA via its stem loop II and facilitate the splicing process. In contrast, little is known about the potential function of U1Ap C-terminal RRM domain 2 (RRM2) despite similar characteristics to other RNA binding domains including U1Ap RRM1. U1Ap RRM2 exhibits unusual RNA binding properties because it does not bind to U1, U2, or U5 stem loops or interact with random RNA sequences.

Autoimmune responses to U1 snRNP specific proteins, including U1Ap, have been described in patients diagnosed with SLE and MCTD. In some cohorts, anti-U1Ap responses have been reported to be the first anti-U1-snRNP to develop.

Clinically, kidney damage is more frequent in SLE while lung malfunction is often observed in MCTD patients.

Previous studies have described elevated IgG autoimmune response to U1Ap fragments in both SLE and MCTD patients. In addition, SLE but not MCTD patients show a predominant immunoglobulin M (IgM) response to snRNP subunits, including U1Ap. Interestingly, while the immune response for U1A and U1 snRNP peptides mature from IgM to IgG in MCTD patients, SLE patients appear to retain IgM responses for these auto-antigens.

BRIEF SUMMARY

The subject invention provides methods for identifying the presence or an increased risk of developing organ damage in a subject having an autoimmune disease or other disease in which the lungs and/or kidneys are involved. In specific embodiments, the autoimmune disease is Systemic Lupus Erythematosus (SLE) or Mixed Connective Tissue Disease (MCTD). In specific embodiments, the disease is fibrosis, such as lung fibrosis, or cancer.

In preferred embodiments, the method of the invention involves detecting the levels of IgM antibodies against certain U1A peptides in a biological sample, such as blood, taken from a subject. The sample can be obtained from a subject having or suspected to have, an autoimmune disease such as, for example, SLE or MCTD. The levels of IgM antibodies against the U1Ap epitopes can be used to predict the presence of, or risk of developing, organ damage, for example kidney damage or lung damage.

Methods of treating and/or preventing the organ damage are also provided.

In specific embodiments, the diagnostic methods of the subject invention comprise determining the levels of IgM antibodies against at least three peptides selected from the peptides having the sequences of SEQ ID NOs: 4, 9, 12, and 15 in a sample (including blood) obtained from the subject and optionally, in a control sample, comparing the combined level of IgM antibodies in the test sample with that of the control sample or a reference value and identifying the subject as having lung damage or an increased risk of developing lung damage, based on the comparison of the combined level of IgM antibodies in the test sample with that of the control sample or a reference value.

In further specific embodiments, the methods of identifying the presence of, or an increased risk of developing, kidney damage in a subject having, for example, SLE or MCTD comprise detelinining the levels of IgM antibodies against at least three peptides selected from the peptides having the sequences of SEQ ID NOs: 2, 8, 12, 14, 15, and 17 in a sample (including blood) obtained from the subject and optionally, in a control sample, comparing the combined level of IgM antibodies in the test sample with that of the control sample or a reference value and identifying the subject as having lung damage or an increased risk of developing lung damage, based on the comparison of the combined level of IgM antibodies in the test sample with that of the control sample or a reference value.

In certain embodiments, the invention provides assays and kits for detecting levels of IgM antibodies against U1Ap epitopes. The kits can comprise peptides representing certain epitopes of U1Ap, optionally adsorbed on a matrix. The kit may also comprise secondary antibodies to detect binding of IgM antibodies from the patient with the epitopes linked to the plate. Additionally, the kit can comprise reagents for blocking, reagents for the preparation of samples, reagents for preparation of reaction mixtures, washing reagents, and reagents for visualization of the binding between the epitopes of U1Ap protein and IgM antibodies.

BRIEF DESCRIPTION OF THE SEQUENCES

SEQ ID NO: 1 shows positions 1-11 of human U1Ap. This sequence represents epitope P1.
SEQ ID NO: 2 shows positions 35-58 of human U1Ap. This sequence represents epitope P2.
SEQ ID NO: 3 shows positions 47-59 of human U1Ap. This sequence represents epitope P3.
SEQ ID NO: 4 shows positions 60-95 of human U1Ap. This sequence represents epitope P4.
SEQ ID NO: 5 shows positions 96-103 of human U1Ap. This sequence represents epitope P5.
SEQ ID NO: 6 shows positions 112-119 of human U1Ap. This sequence represents epitope P6.
SEQ ID NO: 7 shows positions 118-127 of human U1Ap. This sequence represents epitope P7.
SEQ ID NO: 8 shows positions 143-154 of human U1Ap. This sequence represents epitope P8.
SEQ ID NO: 9 shows positions 159-178 of human U1Ap. This sequence represents epitope P9.
SEQ ID NO: 10 shows positions 165-172 of human U1Ap. This sequence represents epitope P10.
SEQ ID NO: 11 shows positions 178-185 of human U1Ap. This sequence represents epitope P11.
SEQ ID NO: 12 shows positions 180-193 of human U1Ap. This sequence represents epitope P12.
SEQ ID NO: 13 shows positions 196-203 of human U1Ap. This sequence represents epitope P13.
SEQ ID NO: 14 shows positions 204-235 of human U1Ap. This sequence represents epitope P14.
SEQ ID NO: 15 shows positions 236-242 of human U1Ap. This sequence represents epitope P15.
SEQ ID NO: 16 shows positions 239-251 of human U1Ap. This sequence represents epitope P16.
SEQ ID NO: 17 shows positions 257-282 of human U1Ap. This sequence represents epitope P17.

DETAILED DISCLOSURE

Figure 1:
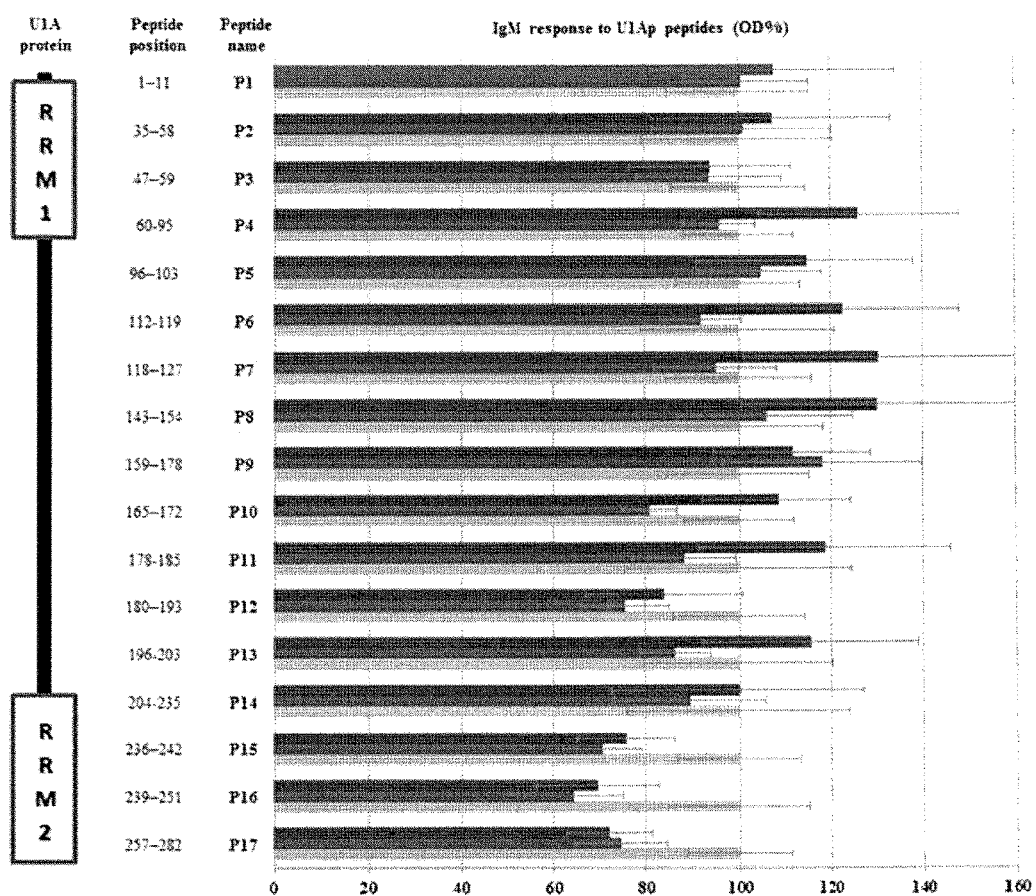
FIG. 1. SLE but not MCTD patients show a predominant IgM response to U1Ap subunits. The U1A protein is represented with a graphical diagram of the linear structure of this protein where RNA recognition motif 1 (RRM1) and 2 (RRM2) are labeled. The amino acids covered by each of the peptides (P1-P17) are indicated under peptide position. The medium grey, dark grey, and light grey columns correspond to IgM reactivity for each of the evaluated peptides in SLE (n=56), MCTD (n=26) and healthy (n=10) individuals, respectively. The error bars represent the standard error.

In one embodiment, the subject invention provides methods for identifying the presence or an increased risk of developing organ damage, for example, with minimal invasive method, for example, a blood sample, in a subject having an autoimmune disease or other disease in which the lungs and/or kidneys are involved. In specific embodiments, the autoimmune disease is Systemic Lupus Erythematosus (SLE) or Mixed Connective Tissue Disease (MCTD). In another specific embodiment, the disease is fibrosis, such as lung fibrosis.

In preferred embodiments, the method of the subject invention comprises detecting the levels of IgM antibodies against certain U1A peptides in a biological sample taken from a patient including blood. The sample can be from, for example, a subject having or at risk for having, an autoimmune disease such as, for example, SLE or MCTD as well as other maladies including cancer. The levels of IgM antibodies against the U1A epitopes can be used to predict the presence or an increased risk of developing organ damage.

In specific embodiments, the diagnostic methods of the subject invention comprise determining the levels of IgM antibodies against at least three peptides selected from the peptides having the sequences of SEQ ID NOs: 4, 9, 12, and 15 in a biological sample, for example a blood sample, obtained from the subject and in a control sample, comparing the combined level of IgM antibodies against the peptides in the test sample and the control sample and identifying the subject as having lung damage, or an increased risk of developing lung damage based on the comparison of the combined level of IgM antibodies against the peptides in the test sample and the control sample.

In further specific embodiments, the methods of identifying the presence of, or an increased risk of developing, kidney damage in a subject having, for example, SLE or MCTD comprise determining the levels of IgM antibodies against at least three peptides selected from the peptides having the sequences of SEQ ID NOs: 2, 8, 12, 14, 15, and 17 in a biological sample, for example a blood sample, obtained from the subject and in a control sample, comparing the combined level of IgM antibodies in the test sample and the control sample and identifying the subject as having kidney damage, or significantly increased risk of developing kidney damage based on the comparison of the combined level of IgM antibodies against the peptides in the test sample and the control sample.

In certain embodiments, a subject identified as having or being at an increased risk of having organ damage is treated to prevent or retard such organ damage.

In certain embodiments, the invention provides assays and kits for detecting levels of IgM antibodies against U1Ap epitopes. The kits can comprise peptides representing certain epitopes of U1Ap, optionally adsorbed on a matrix. The kit may also comprise secondary antibodies to detect binding of IgM antibodies with the epitopes. Additionally, the kit can comprise reagents for blocking, reagents for the preparation of samples, reagents for preparation of reaction mixtures, washing reagents, and reagents for visualization of the binding between the epitopes of U1Ap protein and IgM antibodies.

Methods of treating and/or preventing the organ damage existing or predicted to develop in a subject by administering a therapeutic and/or prophylactic treatment to the subject identified as having the organ damage, or having increased risk of developing the organ damage, are also provided.

The sample can be a biological fluid of a subject. Non-limiting examples of biological fluid samples include aqueous humor, vitreous humor, blood serum, blood plasma, urine, saliva, tears, cerebrospinal fluid, exudates, lymph, mucus, pericardial fluid, pleural fluid, or synovial fluid. The sample can also be a tissue sample of the subject. Non-limiting examples of tissue samples include thyroid gland, parathyroid glands, heart biopsy, lung biopsy, thymus gland, kidney, adrenal glands, appendix, gall bladder, urinary bladder, large intestine, small intestine, liver, pancreas, spleen, prostate, testes, ovaries, or uterus. Various methods of processing samples and isolating IgM antibodies from the tissue samples are well known to a person with ordinary skill in the art.

The methods of determining levels of IgM antibodies against one or more U1Ap epitopes include competitive assays, non-competitive assays, homogenous assays, or heterogeneous assays. Non-limiting examples of assays used to determine the levels of IgM antibodies in a sample include enzyme linked immunosorbent assay (ELISA), radio-immuno assay (RIA), fluorescence-immunoassay (FIA), peptide microarray analysis, or affinity chromatography. Additional examples of methods for determining levels of IgM antibodies in a sample are well known to a person of ordinary skill in the art and such embodiments are within the purview of the current invention.

Definitions

The term "subject," as used herein, describes an organism, including mammals such as primates, from which a biological sample is obtained and to which treatment and/or prophylaxis can be provided based on the identification of the presence or risk for organ damage or presence of SLE or MCTD. Mammalian species that can benefit from the disclosed methods of treatment include, but are not limited to, humans, apes, chimpanzees, orangutans, humans, monkeys, dogs, cats, horses, cattle, pigs, sheep, goats, chickens, mice, rats, guinea pigs, and hamsters.

In some cases, the methods of the invention can be used in experimental animals, in veterinary application, and in the development of vertebrate models for disease, including, but not limited to, rodents including mice, rats, and hamsters; birds, fish reptiles, and primates.

The term "matrix" refers to any rigid or semi-rigid support onto which an adsorbent can be attached or deposited and to which peptides can be bound. Matrix can be membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Adsorbent" refers to any material capable of adsorbing another material, for example, a peptide. The term "adsorbent" is used herein to refer both to a single material ("monoplex adsorbent") (e.g., a compound or functional group) to which the peptide is exposed, and to a plurality materials ("multiplex adsorbent") to which the peptide is exposed. The adsorbent materials in a multiplex adsorbent are referred to as "adsorbent species." For example, an addressable location on a matrix can comprise a multiplex adsorbent characterized by many different adsorbent species (e.g., anion exchange materials, metal chelators, or antibodies), having different binding characteristics. Matrix material itself can also contribute to adsorbing a peptide and may be considered part of an "adsorbent."

"Adsorption" or "retention" refers to the detectable binding between an absorbent and a peptide either before or after washing with an eluent (selectivity threshold modifier) or a washing solution.

The terms "peptide" and "protein" are used interchangeably herein to refer to amino acid chains of any length, including full length proteins.

The term "antibody" refers to a peptide or a fragment thereof that specifically binds to an epitope. Antibodies can be of any isotype, including IgG, IgA, IgE, IgD, and IgM.

"Specific binding" or "specificity" refers to the ability of an antibody or other agent to exclusively bind to an epitope presented on an antigen or peptide while having relatively little non-specific affinity with other proteins or peptides. Specificity can be determined by, for example, binding or competitive binding assays. Specificity can be mathematically calculated by, e.g., an about 10:1, about 20:1, about 50:1, about 100:1, 10.000:1 or greater ratio of affinity/avidity in binding to the specific antigen or peptide versus nonspecific binding to other molecules.

"Immunoassay" is an assay that uses an antibody to specifically bind to an antigen or other peptide. The immunoassay is characterized by the use of specific binding properties of a particular antibody to a particular antigen or other peptide to isolate, target, and/or quantify the target. Preferably, the antibodies bind to a target protein or peptide at least about two times the background and do not substantially bind in a significant amount to other proteins or peptides present in the sample. Typically a specific or selective reaction will be at least twice background signal or noise and more typically more than 10 to 100 times background.

The sample from the subject can be any suitable sample. The antibody-peptide complex can be detected by any suitable manner. "Detectable moiety" or a "label" refers to any suitable label known in the art, such as a composition detectable by spectroscopic, photochemical, biochemical, immunochemical, or chemical means. The peptides described herein are utilizable as labeled molecules employed in radioimmunoassay (RIA) or enzyme immunoassay (EIA), particularly enzyme linked immunosorbent assay (ELISA), by introducing thereto radioactive substances such as $I^{125}$, $I^{131}$, $H^3$, (tritium), $C^{14}$, chromogenic or fluorescent substances and quantifying the radioactive, chromogenic, or fluorescent signal by, e.g., scintillation counting, densitometry, or flow cytometry; and as molecules conjugated to various enzyme reagents such as peroxidase (PDX), chymotrypsinogen, procarboxypeptidase, glyceraldehyde-3-phosphate dehydrogenase, amylase, phosphorylase, DNase, P-Nase, glucose-6-phosphate dehydrogenase, ornithine decarboxylase, and the like.

The tem "kit" refers to a kit, for example, for diagnosis of an autoimmune disease, for example, SLE or MCTD, and/or prediction of risk to develop organ damage, for example, kidney or lung damage, in a subject having or being suspected of having an autoimmune disease. Optionally, the kit may include any material useful for performing any step of the subject invention as described herein. For instance, the kit may comprise any material useful for determination and/or analysis of levels of antibodies in a biological sample of a subject having or suspected of having, an autoimmune disease, which antibodies bind any of the peptide sequences of SEQ ID NO. 1-17. The kit may also comprise, e.g., a buffering and blocking agent, a preservative, or a stabilizing agent. Each component of the kit is usually enclosed within an individual container and all of the various containers are within a single package along with instructions.

The terms "detecting" or "detect" include assaying or otherwise establishing the presence or absence of antibodies that bind, for example, any of the peptides of SEQ ID NO. 1-17, fragments thereof, or peptides having about 90% to about 99% or more sequence homology to these peptides. The term encompasses quantitative, semi-quantitative, and qualitative detection methodologies. In embodiments of the subject invention involving detection of antibodies, the detection method is preferably an ELISA-based method. Preferably, in the various embodiments of the invention, the detection method provides an indication or output (e.g., readout or signal) with information concerning the presence, absence, or amount of antibodies in a sample from a subject. For example, the output may be qualitative (e.g., "positive" or "negative"), or quantitative (e.g., a concentration such as nanograms per milliliter).

"Detecting" can also include assaying for, interrogating, ascertaining, establishing, or otherwise determining one or more factual characteristics of an autoimmune disease or organ damage. The term encompasses diagnostic, prognostic, and monitoring applications for autoimmune diseases and organ damage, including damage to lungs and kidneys.

The term "significantly" as used in "significantly higher," "significantly increased," "significantly lower" indicates that the difference between the compared values in two (or more) distinct groups is statistically significant. Statistically significant difference is typically expressed in terms of p value and a p value of significantly lower than 0.05 typically indicates a statistically significant difference in the values compared.

Analysis of IgM Responses

Figure 2:
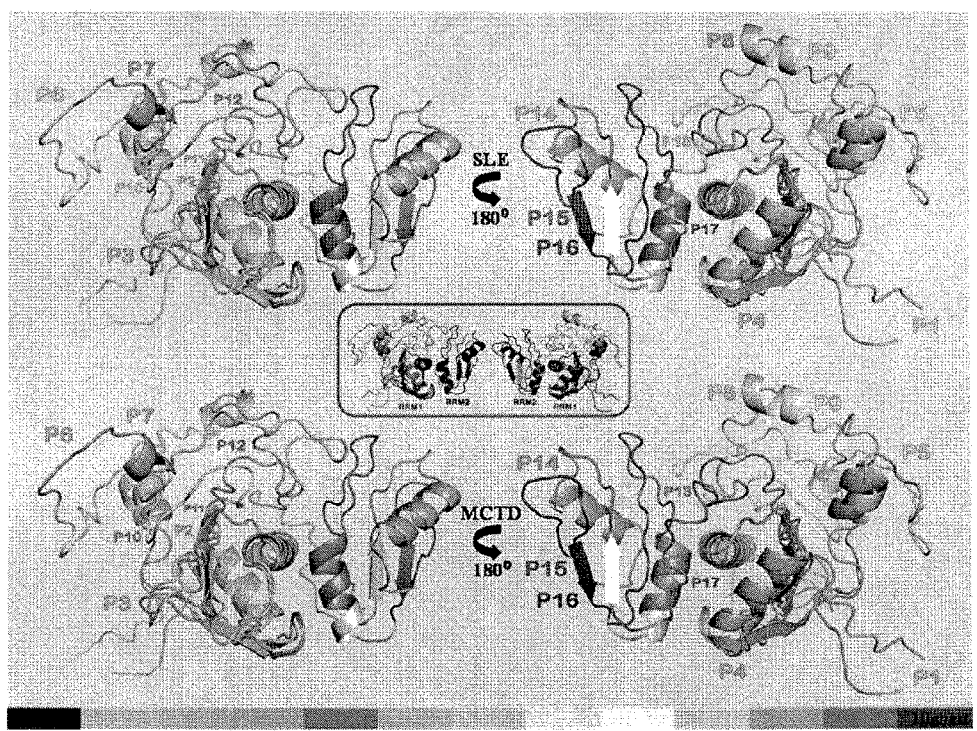
FIG. 2. UTA protein epitope map for IgM antigenicity in SLE and MCTD patients. The IgM optical density percentage (OD %) normalized by the healthy group IgM reactivity for SLE (top) and MCTD (bottom) patients was mapped onto the 3D structure of U1A protein. The IgM antigenic scale is included at the bottom of the figure where blue and red represent the lowest and highest IgM reactivity for U1A protein, respectively. Gray areas on the SLE and MCTD epitope maps correspond to regions of unknown IgM antigenicity since no peptide covers these specific fragments. The rectangle embedded in the middle represents the U1A protein 3D structure where RNA recognition motif 1 (RRM1), RNA recognition motif 2 (RRM2), and the regions free of RNA and protein interactions are indicated in medium grey, darker grey, and lighter grey, respectively.

The mapping of IgM response onto a predicted 3D structure of the full length U1Ap is a unique approach to examining the autoimmune reaction for this protein in SLE and MCTD patients (FIG. 2) U1Ap fragments that do not participate in protein or RNA binding show the highest IgM antigenicity in both SLE and MCTD (P5-P13 in FIGS. 1 and 2). Unbound regions of U1Ap are not sufficient to elicit IgM antigenicity.

Contrary to common belief that antigenic fragments are located on superficial protein regions, the IgM response to U1Ap does not appear to rely only on peptide accessibility on the intact form of the protein.

SLE and MCTD patients' sera were unable to produce an autoimmune reaction for U1Ap RRM2 (P14-P17 in FIGS. 1 and 2) when compared to U1Ap RRM1 (P1-P4). This can be because the RRM2 sequence differs by 78% from that of RRM1 and its binding capacity has been shown to not resemble that of a typical RNA binding protein. The 3D epitope map provided herein allows for visualization of the IgM antigenicity of U1Ap fragments based on their location and molecular structure (FIG. 2).

To examine the IgM responses to U1Ap as a molecular indicator to assess differences between different autoimmune diseases, for example, SLE and MCTD, and to uncover potential relevance of anti-U1Ap IgM reactivity in predicting organ damage in subjects suffering from an autoimmune disease, 17 U1Ap peptides encompassing most of the protein's sequence were monitored for their IgM antigenicity in sera from SLE and MCTD patients with or without kidney and/or lung damage.

Figure 3:
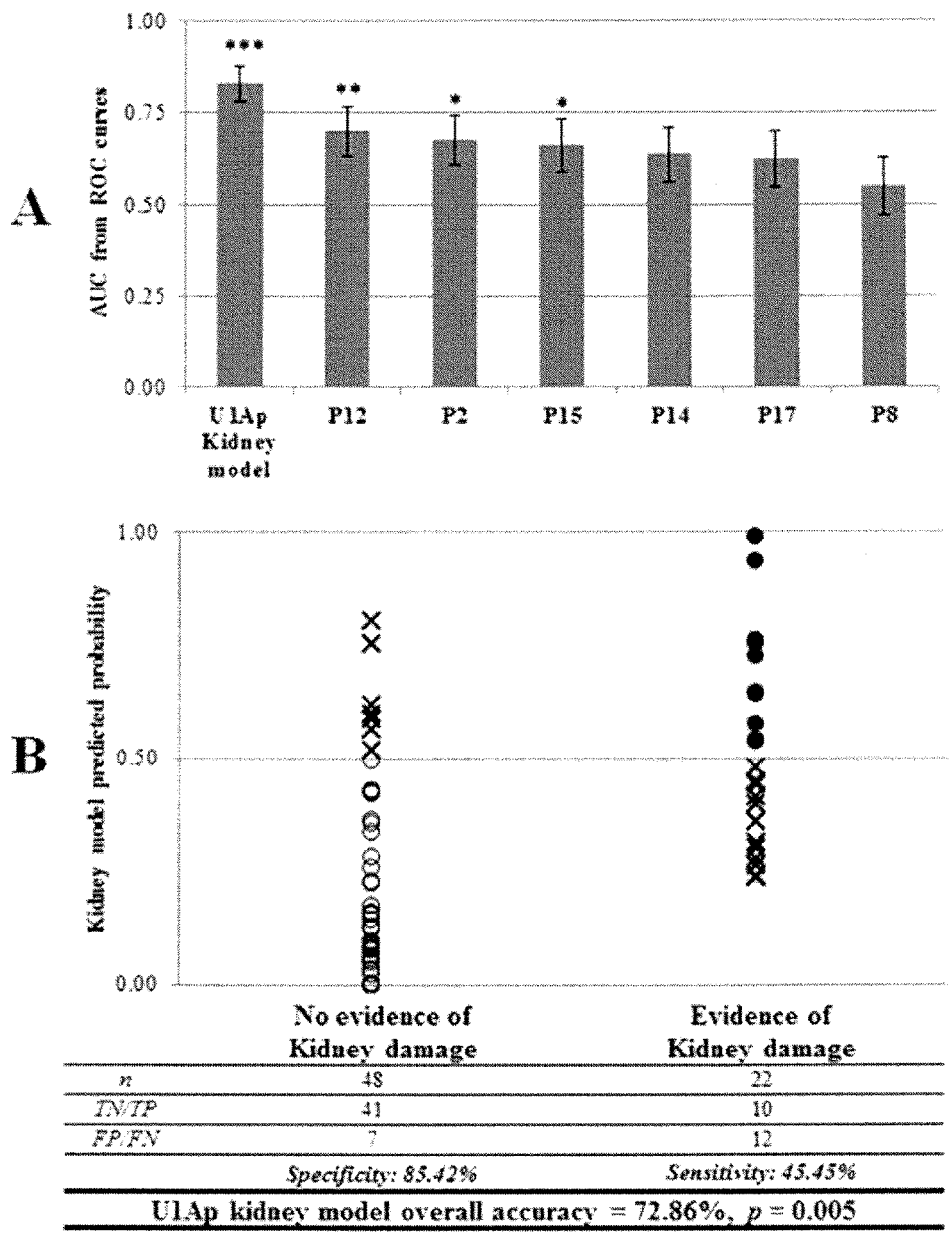
FIG. 3. IgM reactivity for U1Ap is a candidate marker for kidney damage. The observed IgM response to U1A protein (U1Ap) peptides was analyzed by binomial logistic regression (BLR) to assess which peptide combination increases could significantly identify patients with kidney damage in either SLE or MCTD populations ($p \leq 0.05$). The classification ability of each of these peptides and predicted models were corroborated by receiving operating characteristic (ROC) curves analysis ($p \leq 0.05$). A. ROC curves revealed the power of UM peptides in classing patients with kidney damage. In the graph, the peptides and predicted U1Ap kidney model are on the x axis while the area under the curve (AUC) resulting from ROC curves analysis is indicated on the y axis. The larger the number, the significantly higher the probability of identifying an individual with kidney disease compared to a healthy individual. Only peptides with above average predicted power (AUC>0.5) for kidney damage were included. The lines on top of each column correspond to error bars. The p values$\leq 0.05$, $\leq 0.001$ and $0.0001$ are represented with one (*), two () or three (*) asterisks, respectively. B. Distribution of patients with kidney damage based on the U1Ap kidney model. Patients with evidence of kidney damage and healthy individuals are on the x axis while the predicted probabilities obtained from BLR analysis are on the y axis. The black and white dots indicate true positive (TP) and true negatives (TN) while the crosses represent either false positives (FP) or false negatives (FN). A cut off value of 0.5 (from a range of 0 to 1) was selected to allow equal chances to FP and FN ($p \leq 0.05$).

The combined IgM reactivity of six U1Ap peptides (P2, P8, P12, P14, P15 and P17) based on binomial regression analysis facilitated the detection of kidney damage in either SLE or MCTD patients with an overall accuracy of 72% ($p \leq 0.005$) (FIG. 3). Levels of IgM antibodies against certain U1Ap epitopes can be used as an indicator of kidney damage in subjects having or suspected of having, an autoimmune disease such as, for example, SLE or MCTD. Thus, IgM reactivity against certain U1Ap epitopes is provided as a predictive serological biomarker for kidney damage, particularly, in patients suffering from, or expected to be suffering from, an autoimmune disease, for example, SLE or MCTD.

Figure 4:
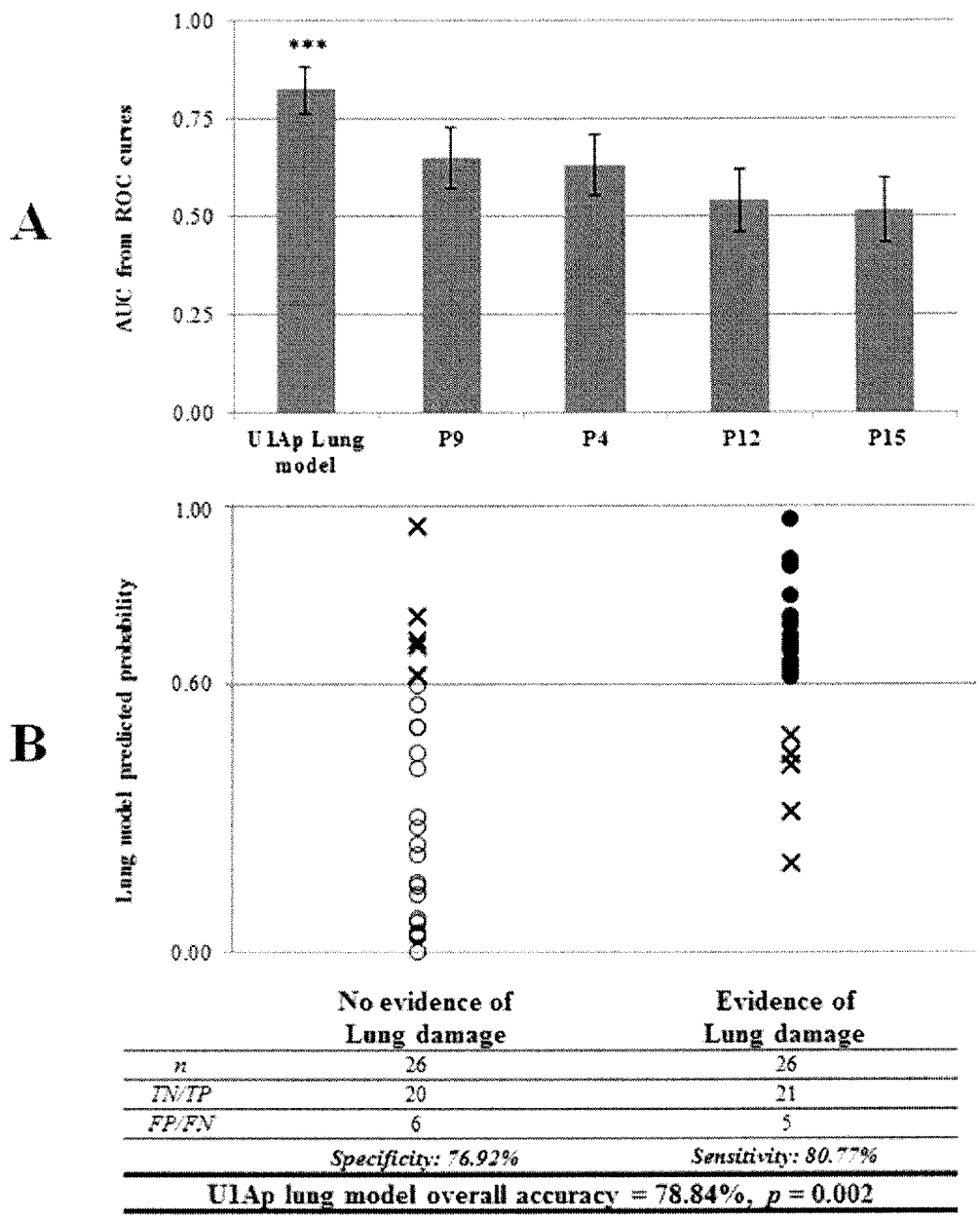
FIG. 4. IgM anti-U1Ap titers are potential biomarkers for lung damage. The IgM reaction for U1A protein (U1Ap) peptides was analyzed by binomial logistic regression (BLR) to uncover peptide combinations with power to discern between patients with lung damage and healthy individuals in either SLE or MCTD populations ($p \leq 0.05$). The grouping capability of each of these peptides and predicted models were corroborated by receiving operating characteristic (ROC) curves analysis ($p \leq 0.05$) A. ROC curves showed the classification power of the U1Ap lung model. In the graph, the peptides and predicted U1Ap lung model and area under the curve (AUC) resulting from ROC curves analysis are on the x and y axes. The bigger the AUC, the highest the classification power for lung disease. Only peptides with above average predicted power (AUC>0.5) for lung damage were included. The lines on top of each column correspond to error bars. The asterisks (***) represent $p \leq 0.0001$. B. Segregation of patients with lung damage utilizing the U1Ap lung model as classifier. In the plot, patients and predicted probabilities of kidney damage are on the x and y axes. The black and white dots indicate true positive (TP) and true negatives (TN), respectively, while the crosses represent either false positives (FP) or false negatives (FN). A cut off value of 0.5 (from a range of 0 to 1) was selected to allow equal chances to FP and FN ($p \leq 0.05$).

In another embodiment, combined IgM reactivity for four U1Ap peptides (P4, P9, P12, and P15) based on binomial regression analysis facilitated the detection of lung damage diagnosed with either SLE or MCTD with an overall accuracy of 79% ($p \leq 0.002$) (FIG. 4). IgM reactivity to specific U1Ap epitopes can be used to identify patients with lung damage. Consequently, levels of IgM antibodies against certain U1Ap epitopes can also be used as an indicator of lung damage in subjects suffering from, or expected to be suffering from, an autoimmune disease, for example, SLE or MCTD.

The invention provides two serological markers for identifying kidney and lung damage in patients having or suspected of having an autoimmune disease, for example, SLE or MCTD (FIGS. 3 and 4).

Lung Damage

One embodiment of the invention provides methods for identifying the presence or an increased risk of developing lung damage in a subject having SLE or MCTD. An increased risk of developing lung damage as used herein, refers to an increased risk of developing lung damage as compared to a subject having SLE or MCTD and known to have no risk or a low risk of developing lung damage within, for example, about 6 months to about 5 years, within about 1 year to about 4 years, within about 2 years to about 3 years.

The method of identifying the presence or an increased risk of developing lung damage in a subject having or expected to develop SLE or MCTD comprises:

a) obtaining a test sample from the subject and optionally obtaining a control sample or a reference value corresponding to combined levels of IgM antibodies against at least three peptides selected from the peptides having the sequences of SEQ ID NOs: 4, 9, 12, and 15, b) determining the level of IgM antibodies against the at least three peptides selected from the peptides having the sequences of SEQ ID NOs: 4, 9, 12, and 15 in the test sample and in the control sample if obtained, c) comparing the combined level of IgM antibodies in the test sample to the reference value or to that of the control sample, and d) identifying the subject as having lung damage or an increased risk of developing lung damage based on the combined level of IgM antibodies in the test sample as compared to that of the control sample or the reference value and optionally, administering a therapy to the subject to treat the lung damage; or e) identifying the subject as not having lung damage or having a low risk or no risk of developing lung damage based on the combined level of IgM antibodies in the test sample as compared to that of the control sample or the reference value and optionally, withholding the therapy to the subject to treat the lung damage.

The step of administering a therapy to treat the lung damage in a subject identified as having lung damage or having an increased risk of developing lung damage provides a tangible result of treating subjects on an individualized basis. Such individualized treatment provides for effective treatment of subjects identified as having lung damage or having an increased risk of developing lung damage.

The step of withholding a therapy to treat the lung damage in a subject identified as not having lung damage or having a low risk or no risk of developing lung damage provides a tangible result of avoiding unnecessary therapies on an individualized basis. Such individualized withholding of treatment avoids adverse side effects of therapies against lung damage where the therapies are not necessary to the subjects identified as not having lung damage or having a low risk or no risk of developing lung damage.

A control sample can be obtained from, for example:

a) an organism belonging to the same species as the subject, wherein the organism is suffering from SLE or MCTD and has lung damage or is known to have an increased risk of developing lung damage;

b) an organism belonging to the same species as the subject, wherein the organism is suffering from SLE or MCTD and does not have lung damage or is known to have no risk or a low risk of developing lung damage;

c) the subject when the subject did not have lung damage or was known to have no risk or low risk of developing lung damage;

d) a sample having a known/predetermined combined level of IgM antibodies against the peptides, wherein the known/predetermined combined level of IgM antibodies is associated with the absence, no risk or low risk of developing lung damage or is associated with the presence or an increased risk of developing lung damage; or e) a healthy organism belonging to the same species as the subject and not suffering from SLE, MCTD or other autoimmune syndrome.

The reference values corresponding to the combined levels of IgM antibodies may indicate no risk or low risk of developing lung damage or an increased risk of development of lung damage. As such, the reference values corresponding to the combined levels of IgM antibodies may indicate the absence or presence of the risk of developing lung damage.

A reference value associated with the absence or no risk or low risk of developing lung damage may be obtained based on samples obtained from subjects known to have the absence or no risk of low risk of developing lung damage. A reference value associated with the presence or an increased risk of developing lung damage may be obtained based on samples obtained from subjects having lung damage or known to have an increased risk of developing lung damage. A subject can be identified as having an increased risk or a low risk or no risk of developing lung damage based on the comparison between combined levels of IgM antibodies against at least three peptides selected from the peptides having the sequences of SEQ ID NOs: 4, 9, 12, and 15 in the test sample and the reference value.

When a control sample is used, the step of identifying the subject as having the presence or an increased risk of developing lung damage or the absence or no risk or low risk of developing lung damage depends on the combined level antibodies against at least three peptides selected from the peptides having the sequences of SEQ ID NOs: 4, 9, 12, and 15 in the test sample as compared to that of the control sample. For example, if the combined level IgM antibodies against at least three peptides selected from the peptides having the sequences of SEQ ID NOs: 4, 9, 12, and 15 in the test sample is significantly higher than the combined level of corresponding IgM antibodies in the control sample which represents the absence of lung damage, the subject is identified as having lung damage or having an increased risk of development of lung damage. Also, if the combined level IgM antibodies against at least three peptides selected from the peptides having the sequences of SEQ ID NOs: 4, 9, 12, and 15 in the test sample is similar, significantly higher or not significantly lower than the combined level of corresponding IgM antibodies in the control sample which represents the presence of lung damage, the subject is identified as having an increased risk of development of lung damage.

A person of ordinary skill in the art can design appropriate comparison between the test sample and the control sample or the reference value to identify a subject as having the presence or an increased risk or the absence or a low risk or no risk of development of lung damage and such embodiments are within the purview of the invention.

In one embodiment, the combined IgM reactivity against the peptides having the sequences of from SEQ ID NOs: 4, 9, 12, and 15, or variants thereof, is compared between the test sample and the control sample which represents absence of lung damage, wherein a significantly increased combined IgM reactivity against the peptides having the sequences of SEQ ID NOs: 4, 9, 12, and 15 or variants thereof, indicates that the subject has lung damage or has an increased risk of developing lung damage.

In another embodiment, the comparison between the combined levels of IgM antibodies against the peptides having the sequences of SEQ ID NOs: 4, 9, 12, and 15, or variants thereof, from the test sample and the control sample is performed by multivariable analysis, for example, multiple regression analysis. Non-limiting examples of multiple regression analysis include BLR, linear regression, logistic regression, and Cox proportional hazards regression analysis.

The variant peptide can have about 90% to about 99% or more sequence identity to SEQ ID NOs: 4, 9, 12, or 15.

Kidney Damage

One embodiment of the invention provides methods for identifying the presence or an increased risk of developing kidney damage in a subject suffering from SLE or MCTD. An increased risk of developing kidney damage as used herein, refers to an increased risk of developing kidney damage as compared to a subject suffering from SLE or MCTD and known to have no risk or a low risk of developing kidney damage within, for example, about 6 months to about 5 years, within about 1 year to about 4 years, within about 2 years to about 3 years.

The methods of identifying the presence or an increased risk of developing, kidney damage in a subject having or expected to develop SLE or MCTD comprise:

a) obtaining a test sample from the subject and optionally obtaining a control sample or a reference value corresponding to combined levels of IgM antibodies against at least three peptides selected from the peptides having the sequences of SEQ ID NOs: 2, 8, 12, 14, 15, and 17, b) determining the level of IgM antibodies against the at least three peptides selected from the peptides having the sequences of SEQ ID NOs: 2, 8, 12, 14, 15, and 17 in the test sample and in the control sample if obtained, c) comparing the combined level of IgM antibodies in the test sample to the reference value or to that of the control sample, and d) identifying the subject as having kidney damage or an increased risk of developing kidney damage based on the combined level of IgM antibodies in the test sample as compared to that of the control sample or the reference value and optionally, administering a therapy to the subject to treat the kidney damage; or e) identifying the subject as not having kidney damage or having a low risk or no risk of developing kidney damage based on the combined level of IgM antibodies in the test sample as compared to that of the control sample or the reference value and withholding the therapy to the subject to treat the kidney damage.

The step of administering a therapy to treat the kidney damage in a subject identified as having kidney damage or having an increased risk of developing kidney damage provides a tangible result of treating subjects on an individualized basis. Such individualized treatment provides for effective treatment of subjects identified as having kidney damage or having an increased risk of developing kidney damage.

The step of withholding a therapy to treat the kidney damage in a subject identified as not having kidney damage or having a low risk or no risk of developing kidney damage provides a tangible result of avoiding unnecessary therapies on an individualized basis. Such individualized withholding of treatment avoids adverse side effects of therapies against kidney damage where the therapies are not necessary to the subjects identified as not having kidney damage or having a low risk or no risk of developing kidney damage.

A control sample can be obtained from, for example:

a) an organism belonging to the same species as the subject, wherein the organism is suffering from SLE or MCTD and has kidney damage or is known to have an increased risk of developing kidney damage;

b) an organism belonging to the same species as the subject, wherein the organism is suffering from SLE or MCTD and does not have kidney damage or is known to have no risk or a low risk of developing kidney damage;

c) the subject when the subject did not have kidney damage or was known to have no risk or low risk of developing kidney damage;

d) a sample having a known/predetermined combined level of IgM antibodies against the peptides, wherein the known/predetermined combined level of IgM antibodies is associated with the absence, no risk or low risk of developing kidney damage or is associated with the presence or an increased risk of developing kidney damage; or e) a healthy organism belonging to the same species as the subject and not suffering from SLE, MCTD or other autoimmune syndrome.

The reference values corresponding to the combined levels of IgM antibodies may indicate no risk or low risk of developing kidney damage or an increased risk of developing kidney damage. As such, the reference values corresponding to the combined levels of IgM antibodies may indicate the absence or presence of the risk of developing kidney damage.

A reference value associated with the absence, no risk or low risk of developing kidney damage may be obtained based on samples obtained from subjects known to have the absence or no risk of low risk of developing kidney damage. A reference value associated with the presence or an increased risk of developing kidney damage may be obtained based on samples obtained from subjects known to have the presence or an increased risk of developing kidney damage. A subject can be identified as having the presence or an increased risk or the absence, a low risk or no risk of developing kidney damage based on the comparison between combined levels of IgM antibodies against at least three peptides selected from the peptides having the sequences of SEQ ID NOs: 2, 8, 12, 14, 15, and 17 in the test sample and the reference value.

When a control sample is used, the step of identifying the subject as having the presence or an increased risk or having the absence or low risk or no risk of developing kidney damage depends on the combined level antibodies against at least three peptides selected from the peptides having the sequences of SEQ ID NOs: 2, 8, 12, 14, 15, and 17 in the test sample as compared to that of the control sample. For example, if the combined level IgM antibodies against at least three peptides selected from the peptides having the sequences of SEQ ID NOs: 2, 8, 12, 14, 15, and 17 in the test sample is significantly higher than the combined level of corresponding IgM antibodies in the control sample which represents the absence of kidney damage, the subject is identified as having an increased risk of development of kidney damage. Also, if the combined level IgM antibodies against at least three peptides selected from the peptides having the sequences of SEQ ID NOs: 2, 8, 12, 14, 15, and 17 in the test sample is similar, significantly higher or not significantly lower than the combined level of corresponding IgM antibodies in the control sample which represents the presence of kidney damage, the subject is identified as having an increased risk of development of kidney damage.

A person of ordinary skill in the art can design appropriate comparison between the test sample and the control sample or the reference value to identify a subject as having an increased risk or a low risk or no risk of development of kidney damage and such embodiments are within the purview of the invention.

In one embodiment, the combined IgM reactivity against the peptides having the sequences of SEQ ID NOs: 2, 8, 12, 14, 15, and 17, or variants thereof, is compared between the test sample and the control sample which represents absence of kidney damage, wherein an increased combined IgM reactivity against the peptides having the sequences of SEQ ID NOs: 2, 8, 12, 14, 15, and 17 or variants thereof, indicates that the subject has kidney damage or has an increased risk of developing kidney damage.

In one embodiment, the level of the IgM antibodies against certain U1Ap peptides in a sample from a patient is compared before and after a treatment to monitor the efficacy of the treatment. For example, the IgM anti-U1Ap ELISA kit can be used to access how well the patient is responding to the treatment.

If a patient is responding well to the treatment, the IgM reactivity for U1Ap peptides would be lower in a sample obtained after the treatment when compared to the sample obtained before the treatment. At the end of a successful treatment the levels of IgM antibodies against specific U1Ap peptides in a sample from a treated patient would be similar to the levels present in a sample from a healthy control sample or a reference value.

On the other hand, if the patient is not responding to the treatment, the levels of IgM antibodies against certain U1Ap peptides in a sample obtained from a patient after the treatment when compared to the sample obtained from the patient before the treatment would be similar or higher. In the case where the patient is not responding to the treatment, the treatment can be stopped or manipulated to consider an alternate treatment.

For example, in one embodiment, the level of the IgM antibodies against a group of peptides consisting of SEQ ID NOs: 4, 9, 12, and 15 in a sample from a patient is compared before and after a treatment to monitor the efficacy of the treatment. If a patient is responding well to the treatment, the IgM reactivity against a group of peptides consisting of SEQ ID NOs: 4, 9, 12, and 15 would be lower in a sample obtained after the treatment when compared to the sample obtained before the treatment. At the end of a successful treatment the levels of IgM antibodies against the group of peptides consisting of SEQ ID NOs: 4, 9, 12, and 15 in a sample from a treated patient would be similar to the levels present in a sample from a healthy control sample or a reference value.

On the other hand, if the patient is not responding to the treatment, the levels of IgM antibodies against a group of peptides consisting of SEQ ID NOs: 4, 9, 12, and 15 in a sample obtained from a patient after the treatment when compared to the sample obtained from the patient before the treatment would be similar or higher. In the case where the patient is not responding to the treatment, the treatment can be stopped or manipulated to consider an alternate treatment.

Similarly, in one embodiment, the level of the IgM antibodies against a group of peptides consisting of SEQ ID NOs: 2, 8, 12, 14, 15, and 17 in a sample from a patient is compared before and after a treatment to monitor the efficacy of the treatment. If a patient is responding well to the treatment, the IgM reactivity against a group of peptides consisting of SEQ ID NOs: 2, 8, 12, 14, 15, and 17 would be lower in a sample obtained after the treatment when compared to the sample obtained before the treatment. At the end of a successful treatment the levels of IgM antibodies against the group of peptides consisting of SEQ ID NOs: 2, 8, 12, 14, 15, and 17 in a sample from a treated patient would be similar to the levels present in a sample from a healthy control sample or a reference value.

On the other hand, if the patient is not responding to the treatment, the levels of IgM antibodies against a group of peptides consisting of SEQ ID NOs: 2, 8, 12, 14, 15, and 17 in a sample obtained from a patient after the treatment when compared to the sample obtained from the patient before the treatment would be similar or higher. In the case where the patient is not responding to the treatment, the treatment can be stopped or manipulated to consider an alternate treatment.

Kits and Assay Devices

Certain embodiments of the invention provide kits for carrying out the methods of the invention. The kit can comprise peptides representing certain epitopes of U1Ap, for example, epitopes represented by peptides having sequences of SEQ ID NOs: 1 to 17, optionally adsorbed on a matrix. The kit can further comprise secondary antibodies that can be labeled. Additionally, the kit can comprise reagents for preparation of samples, reagents for preparation of reaction mixtures, washing reagents, and reagents for visualization of the binding between the epitopes of U1Ap protein and IgM antibodies. The results obtain from the kit can be used to detect lung or kidney damage as well as significantly increased risk of developing lung or kidney damage amongst subjects suffering from autoimmune diseases such as SLE or MCTD as well as other inflammatory and metabolic disorders such as cancer and diabetes. Furthermore, the kit can be used to monitor the patient response to a treatment to alleviate or cure lung or kidney damage.

Kits and assay devices of the invention include a kit comprising one or more peptides having sequences of SEQ ID NO: 1 to 17, particularly, a group of peptides consisting of SEQ ID NOs: 4, 9, 12, and 15 or a group of peptides consisting of SEQ ID NOs: 2, 8, 12, 14, 15, and 17. The kit can further comprise reagents for carrying out an ELISA, RIA, or FIA.

One embodiment of the invention further provides a peptide microarray chip comprising, consisting essentially of, or consisting of the peptides corresponding to epitopes of U1Ap proteins, for example, epitopes represented by peptides having sequences of SEQ ID NO: 1 to 17.

In one embodiment, the protein microarray comprises, consists essentially of, or consists of at least three peptides selected from the peptides having the sequences of SEQ ID NOs: 4, 9, 12, and 15. Such peptide microarray chips can be used to detect lung damage or significantly increased risk of developing lung damage amongst subjects suffering from autoimmune diseases such as SLE or MCTD as well as other inflammatory and metabolic disorders such as cancer and diabetes. Furthermore, the peptide microarray chips could be used to monitor the patient response to a treatment to alleviate or cure lung damage In another embodiment, the protein microarray comprises, consists essentially of, or consists of at least three peptides selected from the peptides having the sequences of SEQ ID NOs: 2, 8, 12, 14, 15, and 17. Such peptide microarray chips can be used to detect kidney damage or significantly increased risk of developing kidney damage amongst subjects suffering from SLE or MCTD.

For the purposes of the current invention, a peptide chip refers to a non-naturally occurring collection of peptides, for example, a collection of microscopic peptide spots attached to a solid surface or a matrix. Typically, the collection of peptides are synthesized and attached via surface engineering to a solid surface by a covalent or a non-covalent bond to a chemical matrix, for example, glass slide. A peptide microarray can be a slide with peptides spotted onto it or assembled directly on the surface by in-situ synthesis. Peptides can be synthesized directly on the glass surface. Peptides can be covalently linked through a chemoselective bond leading to peptides with the same orientation for interaction profiling.

In another aspect of the present invention, peptide chips are provided that correspond to a U1Ap epitopes or combination of U1Ap epitopes, for example, epitopes represented peptides having sequences of SEQ ID NOs: 1 to 17, against which a subject produces significantly increased levels of IgM antibodies, wherein the subject can be: a subject suffering from SLE or MCTD, a subject suffering from SLE or MCTD and having kidney damage or having significantly increased risk of developing kidney damage, a subject suffering from SLE or MCTD and having lung damage or having significantly increased risk of developing lung damage.

For the purposes of this invention, the term "a peptide microarray chip consisting essentially of" certain peptides indicates that the microarray chip contains only those peptides against which a subject produces significantly increased levels of IgM antibodies as compared to an appropriate control subject, wherein the subject can be: a subject suffering from SLE or MCTD, a subject suffering from SLE or MCTD and having kidney damage or having significantly increased risk of developing kidney damage, a subject suffering from SLE or MCTD and having lung damage or having significantly increased risk of developing lung damage, and optionally, one or more control peptides. The control peptide can be selected from the peptides that do not indicate the presence, increased risk, the absence, low risk or no risk of developing organ damage.

Materials and Methods

Patient Recruitment

SLE (n=56) and MCTD (n=26) individuals presenting in either outpatient and inpatient settings were recruited. Healthy individuals (n=10) were included as negative controls. The American College of Rheumatology (ACR) classification criteria and the Alarcon Segovia criteria were used to classify patients as having SLE and MCTD, respectively. In cases where both criteria sets were satisfied, patient diagnoses were determined by the chart-documented diagnoses of their clinical rheumatologists. All SLE and MCTD individuals included in this investigation represent well characterized patients and have been subjects of previous studies.

Medical Records Selection

Kidney involvement was defined following the American College of Rheumatology SLE Classification Criteria's renal criterion and/or renal biopsy. Sufficient information was available to make a determination in 70 of the 82 study patients. Kidney involvement was present in 22 patients (19 SLE and 3 MCTD), and was absent in 48 patients (26 SLE and 22 MCTD).

Lung disease was designated to be present if pulmonary fibrosis was confirmed by chest X-ray or CT-scan, or if pulmonary artery pressure by right heart catheterization or right ventricular systolic pressure estimated by echocardiography meter exceeded 40 mmHg. Sufficient information existed to make a determination about lung involvement in 52 patients, of whom 26 patients had lung involvement (SLE=18 and MCTD=8) and 26 did not have lung involvement (SLE=20 and MCTD=6).

Selection and Synthesis of U1Ap Peptides

Auto-antigenic U1Ap peptides known to elicit an IgG autoimmune reaction in SLE patients were obtained and tested for IgM antigenicity. In addition, amino acid sequences corresponding to each of the two RNA recognition motifs (RRMs) were included as peptides (P4 and P14, Table 2). All peptides were commercially synthesized by BioMatik Corporation (Wilmington, Del., USA) and purified by high performance liquid chromatography to ≥90% purity.

TABLE 2

U1A protein peptides characterization

| Peptide Number | Peptide Position | Peptide Sequence | Peptide length | Reference |
|---|---|---|---|---|
| P1 | 1-11 | MAVPETRPNHT | 11 | Barakat et al. (1991) |
| P2 | 35-58 | SQFGQILDILVSRSLKMRGQAFVI | 24 | Barakat et al. (1991) |
| P3 | 47-59 | RSLKMRGQAFVIF | 13 | Arbuckle et al. (1998) |
| P4 | 60-95 | KEVSSATNALRSMQGFPFYDKPMRIQYAKTDSDIIA | 36 | No previously tested |
| P5 | 96-103 | KMKGTFVE | 8 | Poole et al. (2009) |
| P6 | 112-119 | KPKSQETP | 8 | Somarelli et al. (2011) |
| P7 | 118-127 | TPATKKAVQG | 10 | Poole et al. (2009) |
| P8 | 143-154 | GMPPMTQAPRIM | 12 | Poole et al. (2009) |
| P9 | 159-178 | GQPPYMPPPGMIPPPGLAPG | 20 | Poole et al. (2009) |

TABLE 2-continued

U1A protein peptides characterization

| Peptide Number | Peptide Position | Peptide Sequence | Peptide length | Reference |
|---|---|---|---|---|
| P10 | 165-172 | PPPGMIPP | 8 | Talken et al. (2001) |
| P11 | 178-185 | GQIPPGAM | 8 | Somarelli et al. (2011) |
| P12 | 180-193 | IPPGAMPPQQLMPG | 14 | Poole et al. (2009) |
| P13 | 196-203 | PPAQPLSE | 8 | Somarelli et al. (2011) |
| P14 | 204-235 | NPPNHILFLTNLPEETNELMLSMLFNQFPGFK | 32 | No previously tested |
| P15 | 236-242 | EVRLVPGR | 8 | Poole et al. (2009) |
| P16 | 239-251 | LVPGRHDIAFVEF | 13 | Arbuckle et al. (1998) |
| P17 | 257-282 | AGAARDALQGFKITQNNAMKISFAKK | 26 | Barakat et al. (1991) |

Assessing IgM Autoimmune Response for U1A Protein Peptides

Whole blood from SLE (67 samples from 56 patients), MCTD (29 samples from 26 patients) and healthy (11 samples from 10 persons) individuals were obtained at the moment of the recruitment and subsequent follow up visits. Supernatant serum from each patient was diluted 1:100 in phosphate buffered saline (PBS) containing 10 mg/ml bovine serum albumin (BSA) and 0.5 mM phenylmethyl-sulphonyl fluoride (PMSF) and subsequently stored at −80° C. until tested. Diluted sample sera from SLE, MCTD and healthy individuals were used to determine IgM reactivity for U1Ap peptides via indirect-ELISA. Goat anti-human IgM horseradish peroxidase conjugated second antibody (Southern Biotech, Birmingham, Ala., USA) was used at 1:2000 in BSA/PBS containing 0.05% Tween-20 (BSA/PBS-T). All ELISAs were performed in triplicates. Each ELISA plate contained no peptide, no serum, no conjugate and no substrate controls. The optical density (OD) value of the IgM anti-U1Ap titers in each patient was normalized by the average IgM anti-U1Ap reactivity in the healthy group per peptide examined and expressed as OD % following established methods.

Peptides derived from the U1A protein (HUGO gene name SNRPA) were non-covalently linked to an absorbent well. Subsequently, wells were blocked with bovine serum albumin (BSA) diluted in phosphate buffered saline (BSA/PBS) and incubated in the presence of serum from patients with autoimmune diseases. Subsequently, unbound serum antibodies were washed off, and wells were incubated with goat anti-human IgM horseradish peroxidase conjugated secondary antibodies (Southern Biotech, Birmingham, Ala., USA) used at 1:2000 in BSA/PBS containing 0.05% Tween-20 (BSA/PBS-T). Wells were washed, and IgM-specific reactivity against U1A peptides was assessed by adding o-phenylenediamine dihydrochloride substrate and reading wells in a 96-well plate reader at 450 nm. All ELISAs were performed in triplicate. Each ELISA plate contained no peptide, no serum, no conjugate and no substrate controls. The optical density (OD) value of the IgM anti-U1Ap titers in each patient was noinialized by the average IgM anti-U1Ap reactivity in the healthy group per peptide examined and expressed as OD % following established methods. The recorded absorbance values for each of the U1A-derived peptides were analyzed by binomial logistic regressions (BLR) to predict which combination of IgM anti-U1A peptide titers, if any, provided the greatest segregation between subjects with or without kidney involvement or lung disease with p-values less than 0.05 considered statistically significant.

Specifically, kidney involvement was defined following the American College of Rheumatology SLE Classification Criteria's renal criterion and/or renal biopsy. Likewise, lung disease was designated to be present if pulmonary fibrosis was confirmed by chest X-ray or CT-scan, or if pulmonary artery pressure by right heart catheterization or right ventricular systolic pressure estimated by echocardiography meter exceeded 40 mmHg. Originally, a total of 17 peptides derived from U1A protein were tested and the peptide combination(s) with the greatest ability to predict whether patients with autoimmune diseases have lung or kidney damage based on BLR were chosen (p<0.05). The results obtained from the BLR analyses were corroborated by Receiving Operating Characteristic (ROC) curves (p<0.05).

Mapping IgM Response onto U1A Protein 3D Structure in SLE and MCTD Patients

The observed IgM responses for U1Ap peptides in SLE and MCTD patients were mapped independently onto the U1Ap 3D model. To construct the IgM reactivity gradient for each peptide, the average value of the healthy group was adjusted to a baseline of 0.5. Subsequently, the average IgM reactivity recorded in each of the SLE and MCTD groups was expressed as a proportion relative to that baseline. Reactivity significantly lower or significantly higher than the healthy patient averages per peptides resulted in proportional values below or above 0.5, respectively. Based on this proportional value, each peptide was mapped on a heat map with the scale ranging from the lowest antigenicity to the highest antigenicity.

Statistical Analysis

Significant differences in the average peptide antigenicity against IgM, in SLE and MCTD patients were assessed by independent sample t-test. Correlation analyses were performed to verify the IgM responses for U1Ap peptides were not correlated to peptide size (p 5_ 0.05). The Chi-square test was employed to compare categorical variables. Spearman's correlation was employed to assess the association between IgM anti-U1Ap titers and kidney or lung involvement. Binomial Logistic Regression (BLR) was used to assess which combination of IgM reactivity for U1Ap peptides enhanced the discrimination between patients presenting with kidney or lung involvement versus those lacking these manifestations. Peptides that were found to be not significant in BLR analysis were not included in subsequent tests. Receiving Operating Characteristics (ROC) curves were used to confirm results obtained by BLR and determine the cut off values to ensure the best sensitivity and specificity for kidney and lung models which were 0.5 and 0.6, respectively. Statistical analyses were performed using PASW statistical Data Editor, version 18, with $p \leq 0.05$ set as the standard for statistical inference for all the tests executed.

A further embodiment of the invention provides a method for determining the level of IgM antibody against at least one peptide selected from the peptides having the sequences of SEQ ID NOs: 4, 9, 12, and 15 in a test sample from a subject and, optionally, in a control sample, the method comprising:

a) obtaining the test sample from the subject and, optionally, the control sample;

b) detecting the level of IgM antibody against the at least one peptide in the test sample and, optionally, in the control sample, by contacting the test sample and, optionally, the control sample, with the at least one peptide and quantifying the peptide-IgM complex between the at least one peptide and the corresponding IgM antibody.

In an embodiment, the test sample can be obtained from a subject suffering from immune disorder such as SLE or MCTD as well as other inflammatory and metabolic disease such as cancer and diabetes.

In another embodiment, the control sample is obtained from:

a) an organism belonging to the same species as the subject, wherein the organism is suffering from SLE or MCTD and has lung damage or is known to have an increased risk of developing lung damage;

b) an organism belonging to the same species as the subject, wherein the organism is suffering from SLE or MCTD and does not have lung damage or is known to have no risk or a low risk of developing lung damage;

c) the subject when the subject did not have lung damage or was known to have no risk or low risk of developing lung damage;

d) a sample having a known/predetermined combined level of IgM antibodies against the peptides, wherein the known/predetermined combined level of IgM antibodies is associated with the absence, no risk or low risk of developing lung damage or is associated with the presence or an increased risk of developing lung damage; or e) a healthy organism belonging to the same species as the subject and not suffering from SLE, MCTD or other autoimmune syndrome.

The test sample and the control sample can be a biological fluid. Non-limiting examples of biological fluid samples include aqueous humor, vitreous humor, blood serum, blood plasma, urine, saliva, tears, cerebrospinal fluid, exudates, lymph, mucus, pericardial fluid, pleural fluid, or synovial fluid. The test sample and the control sample can also be a tissue sample. Non-limiting examples of tissue samples include thyroid gland, parathyroid glands, heart biopsy, lung biopsy, thymus gland, kidney, adrenal glands, appendix, gall bladder, urinary bladder, large intestine, small intestine, liver, pancreas, spleen, prostate, testes, ovaries, or uterus. Various methods of processing samples and isolating IgM antibodies from the tissue samples are well known to a person with ordinary skill in the art.

In one embodiment, the levels of IgM antibodies against at least three peptides selected from the peptides having the sequences of SEQ ID NOs: 4, 9, 12, and 15 are determined.

A further embodiment of the invention provides a method for determining the level of IgM antibody against at least one peptide selected from the peptides having the sequences of SEQ ID NOs: 2, 8, 12, 14, 15, and 17 in a test sample from a subject and, optionally, in a control sample, the method comprising:

a) obtaining the test sample from the subject and, optionally, the control sample;

b) detecting the level of IgM antibody against the at least one peptide in the test sample and optionally, in the control sample, by contacting the test sample and, optionally, the control sample, with the at least one peptide and quantifying the peptide-IgM complex between the at least one peptide and the corresponding IgM antibody.

In an embodiment, the test sample can be obtained from a subject suffering from SLE or MCTD.

In another embodiment, the control sample is obtained from:

a) an organism belonging to the same species as the subject, wherein the organism is suffering from SLE or MCTD and has kidney damage or is known to have an increased risk of developing kidney damage;

b) an organism belonging to the same species as the subject, wherein the organism is suffering from SLE or MCTD and does not have kidney damage or is known to have no risk or a low risk of developing kidney damage;

c) the subject when the subject did not have kidney damage or was known to have no risk or low risk of developing kidney damage;

d) a sample having a known/predetermined combined level of IgM antibodies against the peptides, wherein the known/predetermined combined level of IgM antibodies is associated with the absence, no risk or low risk of developing kidney damage or is associated with the presence or an increased risk of developing kidney damage; or e) a healthy organism belonging to the same species as the subject and not suffering from SLE, MCTD or other autoimmune syndrome.

The test sample and the control sample can be a biological fluid. Non-limiting examples of biological fluid samples include aqueous humor, vitreous humor, blood serum, blood plasma, urine, saliva, tears, cerebrospinal fluid, exudates, lymph, mucus, pericardial fluid, pleural fluid, or synovial fluid. The test sample and the control sample can also be a tissue sample. Non-limiting examples of tissue samples include thyroid gland, parathyroid glands, heart biopsy, lung biopsy, thymus gland, kidney, adrenal glands, appendix, gall bladder, urinary bladder, large intestine, small intestine, liver, pancreas, spleen, prostate, testes, ovaries, or uterus. Various methods of processing samples and isolating IgM antibodies from the tissue samples are well known to a person with ordinary skill in the art.

In one embodiment, the levels of IgM antibodies against at least three peptides selected from the peptides having the sequences of SEQ ID NOs: 2, 8, 12, 14, 15, and 17 are determined.

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

EXAMPLES

Following are examples that illustrate embodiments and procedures for practicing the invention. These examples should not be construed as limiting.

Example 1

Auto-Antigenic IgM Responses to U1Ap

Indirect ELISAs were employed to assess IgM responses for U1Ap peptides in sera from SLE, MCTD and healthy individuals. In general, SLE patients exhibited significantly higher IgM anti-U1Ap titers when compared to the healthy individuals (P1-P11 and P13, FIG. 1). In contrast, except for P5, P8 and P9, MCTD patients had significantly lower IgM responses to U1Ap peptides than healthy individuals (FIG. 1). Interesting, anti-U1Ap-P16 IgM reactivity was significantly lower in both SLE and MCTD patients compared to healthy controls ($p \leq 0.04$) (FIG. 1). SLE patients showed trends toward significantly higher IgM reactivity for U1Ap subunits than MCTD patients (P4, P6, P7, P10, P11 and P13 were the most antigenic U1Ap fragments against IgM with 1.3 fold significantly higher levels in SLE than MCTD patients), but the differences were not significant ($p > 0.05$, FIG. 1). Specifically, P7 and P17 represented the biggest (137%) and smallest (96%) differences between the SLE and MCTD subsets.

Based on this methodology, it was uncovered that a BLR using IgM-specific reactivity against U1A peptides 4, 9, 12, and 15 significantly segregated SLE or MCTD patients with lung disease from those with normal lung function ($p < 0.001$). This combination of peptides provides the basis for the "lung predictor assay." ROC curves analyses also supported that the "lung predictor assay" has an overall accuracy of 79% with a positive predictive value ("PPV" also known as precision) of 78% and a negative predictive value ("NPV") of 80% ($p < 0.002$). Likewise, the "lung predictor assay" has a sensitivity of 81% and specificity of 77% ($p < 0.002$) (FIG. 4).

Example 2

Auto-Antigenic IgM Response is Directed to Non-RNA Recognition Domain Regions of U1Ap To compare the IgM reactivity in RNA recognition domain versus non-RNA recognition domain fragments of U1Ap, the average peptide reactivity corresponding to regions identified as RNA recognition motif (RRM) 1 (P1-P4), RRM2 (P14-17) and the non-domain area (P4-P13) were calculated in SLE, MCTD and healthy populations. Patients showed elevated IgM anti-U1Ap responses to non-domain areas of the U1Ap (P5-P13) when compared to RRM1 (P1-P4) and RRM2 (P14-P17) (FIG. 1). However, only the SLE and not the MCTD patient subgroup exhibited significantly elevated average IgM response to peptides in U1Ap non-domain regions when compared to the average IgM reactivity for peptides covering RRM1 or RRM2 ($p \leq 0.003$). The IgM response to the U1Ap C-terminal end, which encompasses RMM2, was noticeably significantly lower in both SLE and MCTD patients than in control samples (FIG. 1).

Example 3

IgM Derived U1Ap 3D Epitope Maps for SLE and MCTD Patient

The IgM reactivity for each U1Ap peptide monitored in sera from SLE and MCTD patients was used to create two independent epitope maps of U1Ap (FIG. 2). In general, the IgM reactivity was not always directed to exposed fragments of the U1Ap, given that superficial peptides appeared to have equal chance to be highly antigenic (P7 in SLE and P9 in MCTD) or not (P17 in SLE and P4 in MCTD) (FIG. 2). Likewise, different molecular structures like α-helices (P4), β-sheets (P15) and loops (P8) seemed to elicit antigenic IgM responses to U1Ap. However, β-sheets were the least antigenic of all three forms (P15 and P16 in FIG. 2). When comparing the SLE and MCTD subgroups, significantly higher U1Ap IgM reactivity was directed to superficial peptides with α-helical structure in both SLE (P7) and MCTD (P4) (FIG. 2). The lowest IgM responses were observed for peptides corresponding to exposed β-sheet fragments of the U1Ap in both SLE and MCTD (e.g., P16 in both SLE and MCTD patients in FIG. 2).

Example 4

IgM Anti-U1Ap Titers Discriminate Between Patients with and without Kidney Involvement The IgM responses to specific U1Ap peptides (P2, P8, P12, P14, P15 and P17) across the entire patient group significantly correlated with kidney involvement ($p \leq 0.05$). BLR analyses using all 17 U1Ap peptides confirmed that the combined IgM reactivity for P2, P8, P12, P14, P15 and P17 (referred to as "U1Ap kidney model") represented the best predictor to identify patients with kidney disease ($p \leq 0.0001$) (FIG. 3A). Specifically, ROC analysis confirmed that the U1Ap kidney model had significant power (AUC=0.828) to separate between patients with kidney and without kidney disease with 85% specificity, 45% sensitivity and 73% overall accuracy to correctly categorize patients ($p \leq 0.005$) (FIG. 3B). Furthermore, the analyses revealed that the capacity of the U1Ap kidney model to distinguish an SLE patient with or without kidney disease was not significantly different than that observed in patients with MCTD ($p > 0.05$).

A "kidney predictor assay" was created using the methods described above with IgM-specific reactivity against U1A peptide 2, 8, 12, 14, 15, and 17. This assay exhibits significant power to segregate between autoimmune patients who have clinical evidence of kidney involvement from those with normal renal function ($p < 0.001$). ROC curves confirmed that the "kidney predictor assay" has an overall accuracy of 73% with a PPV of 59% (precision) and a NPV of 77% ($p < 0.005$). Moreover, the "kidney predictor assay" exhibits a sensitivity of 45% and specificity of 85% ($p < 0.005$) (FIG. 3).

Example 5

IgM Anti-U1Ap Reactivity Patterns and Lung Involvement

No anti-U1Ap peptide responses in univariate analyses were found to significantly correlate with lung damage. However, BLR analysis revealed that the combined IgM response to peptides P4, P9, P12 and P15 (the "U1Ap lung model") distinguished between patients with or without lung involvement similarly to the performance of the kidney model above (AUC=0.822) (FIG. 4A). The overall accuracy of the U1Ap lung model to classify patients was 79% with 81% sensitivity 77% specificity (FIG. 4B). As expected, the capacity of the U1Ap lung model to identify a patient with or without lung disease was not significantly different when SLE or MCTD subsets were contrasted.

It should be understood that the examples and embodiments described herein are for illustrative purposes only and that various modifications or changes in light thereof will be suggested to persons skilled in the art and are to be included within the spirit and purview of this application.

REFERENCES

1. Moore, M. J. and Sharp, P. A. (1993) Evidence for two active sites in the splicesome provided by stereochemistry of pre-mRNA. Nature 23:364-368.
2. Scherly D, Boelens W, van Venrooij W J, Dathan N A, Hamm J, Mattaj W (1989) Identification of the RNA binding segment of human U1A protein and definition of its binding site on U1 snRNA. The EMBO J, 8:4163-4170.
3. Chen Y-I G, Moore R E, Ge H Y, Young M K, Lee T D, Stevens S W. 2007. Proteomic analysis of in vivo-assembled pre-mRNA splicing complexes expands the catalog of participating factors. Nucleic Acids Res 35:3928-3944,
4. Somarelli, J A, Mesa A, Fuller M E, Torres J O, Rodriguez C E, Ferrer C M and Herrera R J (2010). Genome-based identification of spliceosomal proteins in the silk moth *Bombyx* mor. Arch of Insect Biochem and Physiol 75:231-263.
5. Jessen T H, Oubridge C, Teo H C, Pritchard C and Nagai K (1991). Identification of molecular contacts between the U1A small nuclear ribonucleoprotein and U1 snRNA. The EMBO J 10:3447-3456.
6. Tang J and Rosbash M (1996). Characterization of yeast U1 snRNP A protein: identification of the N-terminal RNA binding domain (RBD) binding site and evidence that the C-terminal RBD functions in splicing. RNA. 10:1058-1070.
7. Lu J and Hall K B (1995). An RBD that does not bind RNA: NMR secondary structure determination and biochemical properties of the C-terminal RNA binding domain from the human U1A protein. J Mol Biol. 247: 739-752.
8. de Wildt R M, van den Hoogen F H, van Venrooij W J, Hoet R M (1997). Isolation and characterization of single anti-U1A-specific B cells from autoimmune patients. Ann N Y Acad Sci. 815:440-442.
9. McClain M T, Lutz C S, Kaufman K M, Faig O Z, Gross T F, James J A (2004). Structural availability influences the capacity of auto-antigenic epitopes to induce a widespread lupus-like autoimmune response. Proc Natl Acad Sci 101:3551-3556.
10. Faig O Z, Lutz C S (2003). Novel specificity of anti-U1A autoimmune patient sera. Scand J Immunol. 57:79-84.
11. Sato T, Fujii T, Yokoyama T, Fujita Y, Imura Y, Yukawa N, Kawabata D, Nojima T, Ohmura K, Usui T, Mimori T (2010). Anti-U1 RNP antibodies in cerebrospinal fluid are associated with central neuropsychiatric manifestations in systemic lupus erythematosus and mixed connective tissue disease. Arthritis Rheum. 62:3730-3740.
12. Gutsche M, Rosen G D, Swigris J J (2012). Connective Tissue Disease-associated Interstitial Lung Disease: A review. Curr Respir Care Rep. 21:224-232.
13. Braun-Moscovici Y, Butbul-Aviel Y, Guralnik L, Toledano K, Markovits D, Rozin A, Nahir M A, Balbir-Gurman A (2013). Rituximab: rescue therapy in life-threatening complications or refractory autoimmune diseases: a single center experience. Rheumatol Int. 33:1495-1504.
14. Sharp G C, Irvin W S, Tan E M, Gould R G, Holman H R (1972). Mixed connective tissue disease—an apparently distinct rheumatic disease syndrome associated with a specific antibody to an extractable nuclear antigen (ENA). Am J Med 52:148-159.
15. Rebora A, Parodi A (1990). Mixed connective tissue disease and correlated diseases. G Ital Dermatol Venereol. 125:357-362.
16. Swanton J, Isenberg D (2005). Mixed connective tissue disease: Still crazy after all these years. Rheum Dis Clin North Am 31:421-436.
17. Nowicka-Sauer K, Czuszynska Z, Majkowicz M, Smolenska Z, Jarmoszewicz K, Olesinska M, Siebert J (2012). Neuropsychological assessment in mixed connective tissue disease: Comparison with systemic lupus erythematosus. Lupus. 21:927-933.
18. Luyckx A, Westhovens R, Oris E, Papisch W, Bossuyt X (2005). Clinical relevance of measurement of antibodies to individual snU1-RNP proteins. Clin Chem 51:1888-1890.
19. Sawai T, Murakami K, Kurasono Y (1994). Morphometric analysis of the kidney lesions in mixed connective tissue disease (MCTD). Tohoku J Exp Med. 174:141-154.
20. Yoshida A, Morozumi K, Takeda A, Koyama K (1994). Nephropathy in patients with mixed connective tissue disease. Ryumachi. 34:976-980.
21. De Clerck L S, Meijers K A, Cats A (1989). Is MCTD a distinct entity? Comparison of clinical and laboratory findings in MCTD, SLE, PSS, and R A patients. Clin Rheumatol. 8:29-36.
22. Watanabe Y, Koyama S, Moriguchi M, Miwa C, Shiraishi M, Nomura M, Nokubi M, Terai C, Kawabata Y (2012). Rapidly progressive respiratory failure in mixed connective tissue disease: report of an autopsy case. Intern Med. 5:3415-3419.
23. Vlachoyiannopoulos P G, Guialis A, Tzioufas G, Moutsopoulos H M (1996). Predominance of IgM anti-U1RNP antibodies in patients with systemic lupus erythematosus. Br J Rheumatol. 35:534-541.
24. Mesa A, Somarelli J, Wu W, Martinez L, Blom M, Greidinger E, Herrera R (2013). Differential immunoglobulin class-mediated responses to components of the U1 small nuclear ribonucleoprotein particle in systemic lupus erythematosus and mixed connective tissue disease. Lupus. 22:1371-1381.
25. Amigues J M, Cantagrel A, Abbal M and Mazieres B. Comparative study of 4 diagnosis criteria sets for MCTD in patients with anti-RNP antibodies (1996). Autoimmunity group of the hospital of Toulouse. J Rheumatol. 12:2055-2062.
26. Hochberg M C (1997). Updating the America College of Rheumatology revised criteria for the classification of systemic lupus erythematosus. Arthritis Rheum. 40:1725.
27. Maldonado M E, Perez M, Pignac-Kobinger J, Marx E T, Tozman E M, Greidinger E L, Hoffman R W (2008). Clinical and immunologic manifestations of mixed connective tissue disease in a Miami population compared to a Midwestern U S Caucasian population. J Rheumatol. 35:429-437.
28. Perkins K, Hoffman R W, Bezruczko N (2008). A Rasch analysis for classification of systemic lupus erythematosus and mixed connective tissue disease. J Appl Meas. 9:136-50.

29. Somarelli J A, Mesa A, Rodriguez R, Avellan R, Martinez L, Zang Y J, Greidinger E L, Herrera R J (2011). Epitope mapping of the U1 small nuclear ribonucleoprotein particle in patients with systemic lupus erythematosus and mixed connective tissue disease. Lupus. 20:274-289.
30. Barakat S, Briand J P, Abuaf N, Van Regenmortel M H V, Muller S (1991). Mapping of epitopes on U1 snRNP peptide A with synthetic peptides and autoimmune sera. Clin Exp Immunol. 86:71-78.
31. Arbuckle M R, Schilling A R, Harley J B, James J A (1998). A limited lupus anti-spliceosomal response targets a cross-reactive, proline-rich motif. J Autoimmun. 11:431-438.
32. Talken B L, Schafermeyer K R, Bailey C W, Lee D R, Hoffman R W (2001). T cell epitope mapping of the Smith antigen reveals that highly conserved Smith antigen motifs are the dominant target of T cell immunity in systemic lupus erythematosus. J Immunol 167:562-568.
33. Poole B D, Schneider R I, Guthridge J M, Velte C A, Reichlin M, Harley J B, James, J A (2209). Early targets of nuclear RNP humoral autoimmunity in human systemic lupus erythematosus. Arthritis Rheum 60:848-859.
34. Murioz-Paredes J C, Oliveira L G, de Carvalho Braga A, Trevisol I M, Roche P M (1999). Development and standardization of an indirect ELISA for the serological diagnosis of classical swine fever. Pesq Vet Bra 19:123-127.
35. Zhang Y (2008). I-TASSER server for protein 3D structure prediction. BMC Bioinformatics. 9:40.
36. Roy A, Kucukural A, Zhang Y (2010). I-TASSER: a unified platform for automated protein structure and function prediction. Nat Protoc. 5:725-738.
37. Roy A, Yang J, Zhang Y (2012). COFACTOR: an accurate comparative algorithm for structure-based protein function annotation. Nucleic Acids Res. (Web Server issue): W471-7.
38. Sasaki N, Kamataki A, Sawai T (2011). A histopathological study of pulmonary hypertension in connective tissue disease. Allergol Int. 60:411-417.
39. Lage L V, de Carvalho J F, Caleiro M T, Yoshinari N H, da Mota L M, Khamashta M A, Cossermelli W (2012). Fluctuation of anti-endothelial cell antibody titers in "mixed connective tissue disease". Isr Med Assoc J. 14:84-87.
40. Jin L, Weiqian C, Lihuan Y (2013). Peripheral CD24(hi) CD27(+) CD19(+) B cells subset as a potential biomarker in nave systemic lupus erythematosus. Int J Rheum Dis. 16:698-708.
41. Varani L, Gunderson S I, Mattaj I W, Kay L E, Neuhaus D, Varani G (2000). The NMR structure of the 38 kDa U1A protein—PIE RNA complex reveals the basis of cooperativity in regulation of polyadenylation by human U1A protein. Nat Struct Biol. 7:329-335.
42. Migliorini P, Baldini C, Rocchi V, Bombardieri S (2005). Anti-Sm and anti-RNP antibodies. Autoimmunity. 38:47-54.
43. Mevorach D (2003). Systemic lupus erythematosus and apoptosis: a question of balance. Clin Rev Allergy Immunol. 25:49-60.
44. Casciola-Rosen L, Andrade F, Ulanet D, Wong W B, Rosen A (1999). Cleavage by granzyme B is strongly predictive of autoantigen status: implications for initiation of autoimmunity. J Exp Med 190:815-26
45. Yang C C, Hsieh S C, Li K J, Wu C H, Lu M C, Tsai C Y, Yu C L (2012). Urinary neutrophil gelatinase-associated lipocalin is a potential biomarker for renal damage in patients with systemic lupus erythematosus. J Biomed Biotechnol. 2012:759313.
46. Pizarro S, Monarrez Espino J, Ruiz A, Jara Li, Nava A, Riebeling-Navarro C (2007). Soluble vascular cell adhesion molecule-1 indicates SLE disease activity and specific organ involvement. Rev Alerg Mex. 54:189-95.
47. Brugos B, Vincze Z, Sipka S, Szegedi G, Zeher M (2012). Serum and urinary cytokine levels of SLE patients. Pharmazie. 67:411-413.
48. Simón J A, Cabiedes J, Ortiz E, Alcocer-Varela J, Sanchez-Guerrero J (2004). Anti-nucleosome antibodies in patients with systemic lupus erythematosus of recent onset. Potential utility as a diagnostic tool and disease activity marker. Rheumatology. 43:220-224.
49. Haase M, Bellomo R, Devarajan P, Schlattmann P, Haase-Fielitz A; NGAL Meta-analysis Investigator Group (2009). Accuracy of neutrophil gelatinase-associated lipocalin (NGAL) in diagnosis and prognosis in acute kidney injury: a systematic review and meta-analysis. Am J Kidney Dis, 54:1012-1024.
50. Nishimaki T, Aotsuka S, Kondo H, Yamamoto K, Takasaki Y, Sumiya M, Yokohari R (1999). Immunological analysis of pulmonary hypertension in connective tissue diseases. J Rheumatol. 26:2357-2362.
51. Bertoli A M, Vila L M, Apte M, Fessler B J, Bastian H M, Reveille J D, Alarcon G S. LUMINA Study Group (2007). Systemic lupus erythematosus in a multiethnic U S Cohort LUMINA XLVIII: factors predictive of pulmonary damage. Lupus. 16:410-417.
52. Cojocaru M, Cojocaru I M, Silosi I, Vrabie C D (2011). Pulmonary manifestations of systemic autoimmune diseases. Maedica (Buchar). 6:224-229.
53. Zhang L, Liu J, Zhang H, Wu S, Huang L, He D, Xiao X (2005). Discovery and identification of anti-U1-A snRNP antibody in lung cancer. Sci China C Life Sci. 48:641-647.
54. Levitt J E, Calfee C S, Goldstein B A, Vojnik R, Matthay M A (2013). Early acute lung injury: criteria for identifying lung injury prior to the need for positive pressure ventilation. Crit Care Med. 41:1929-1937.
55. Pehlivan O, Inanc M (2010). Pulmonary arterial hypertension related to connective tissue diseases. Anadolu Kardiyol Derg. 1:57-62
56. Allen D, Fischer A, Bshouty Z, Robinson D B, Peschken C A, Hitchon C, El-Gabalawy H, Meyers M, Mittoo S (2012). Evaluating systemic lupus erythematosus patients for lung involvement. Lupus. 12:1316-1325

What is claimed is:

1. A kit comprising one or more peptides, wherein the one or more peptides is/are:
   i) a peptide consisting of SEQ ID NO: 4, and optionally,
   ii) one or more additional peptides each consisting of a sequence selected from SEQ ID NOs: 1 to 3 and 5 to 17.

2. The kit of claim 1, wherein the kit comprises: the peptide consisting of SEQ ID NO: 4, the peptide consisting of SEQ ID NO: 9, the peptide consisting of SEQ ID NO: 12, and the peptide consisting of SEQ ID NO: 15.

3. The kit of claim 2, wherein the one or more peptides are attached to a rigid or semi-rigid support.

4. The kit of claim 3, wherein the rigid or semi-rigid support is a multi-well plate and the kit further comprises a blocking reagent, a washing reagent, a labeled secondary antibody, and a substrate for visualization of the secondary antibody.

5. The kit of claim 4, wherein the multi-well plate is a 96-well plate, the blocking reagent comprises phosphate buffered saline containing bovine serum albumin, and the washing reagent comprises phosphate buffered saline containing polysorbate.

6. The kit of claim 1, wherein the one or more peptides are attached to a rigid or semi-rigid support.

7. The kit of claim 6, wherein the rigid or semi-rigid support is a multi-well plate and the kit further comprises a blocking reagent, a washing reagent, a labeled secondary antibody, and a substrate for visualization of the secondary antibody.

8. The kit of claim 7, wherein the multi-well plate is a 96-well plate, the blocking reagent comprises phosphate buffered saline containing bovine serum albumin, and the washing reagent comprises phosphate buffered saline containing polysorbate.

9. A kit comprising a peptide consisting of SEQ ID NO: 4, a peptide consisting of SEQ ID NO: 9, a peptide consisting of SEQ ID NO: 12, and a peptide consisting of SEQ ID NO: 15, wherein the peptides of SEQ ID NOs: 4, 9, 12, and 15 are attached to a rigid or semi-rigid support.

10. A method of identifying lung damage in a human subject having Systemic Lupus Erythematosus (SLE) or Mixed Connective Tissue Disease (MCTD), the method comprising:
   a) obtaining a test serum or plasma sample from the subject and obtaining a control sample,
   b) determining the levels of IgM antibodies against the peptides consisting of SEQ ID NOs: 4, 9, 12, and 15 in the test sample and in the control sample, wherein said determining comprises contacting the test and the control samples with the kit of claim 2, and
   c) identifying the subject as:
      i) having lung damage based on the combined level of IgM antibodies in the test sample as compared to that of the control sample and optionally, administering a therapy to the subject to treat the lung damage; or
      ii) not having lung damage based on the combined level of IgM antibodies in the test sample as compared to that of the control sample and optionally, withholding the therapy to the subject to treat the lung damage.

11. The method of claim 10, wherein the control sample is obtained from:
   a) a human suffering from SLE or MCTD and having lung damage;
   b) a human suffering from SLE or MCTD and not having lung damage;
   c) the subject when the subject did not have lung damage; or
   d) a healthy human not suffering from SLE, MCTD or other autoimmune syndrome.

12. The method of claim 10, comprising administering to the subject identified as having lung damage a therapy to treat the lung damage.

13. A method of identifying lung damage in a human subject having Systemic Lupus Erythematosus (SLE) or Mixed Connective Tissue Disease (MCTD), the method comprising:
   a) obtaining a test serum or plasma sample from the subject and obtaining a control sample,
   b) determining the levels of IgM antibodies against the peptides consisting of SEQ ID NOs: 4, 9, 12, and 15 in the test sample and in the control sample, wherein said determining comprises contacting the test and the control samples with the kit of claim 9, and
   c) identifying the subject as:
      i) having lung damage based on the combined level of IgM antibodies in the test sample as compared to that of the control sample and optionally, administering a therapy to the subject to treat the lung damage; or
      ii) not having lung damage based on the combined level of IgM antibodies in the test sample as compared to that of the control sample and optionally, withholding the therapy to the subject to treat the lung damage.

14. The method of claim 13, wherein the control sample is obtained from:
   a) a human suffering from SLE or MCTD and having lung damage;
   b) a human suffering from SLE or MCTD and not having lung damage;
   c) the subject when the subject did not have lung damage; or d) a healthy human not suffering from SLE, MCTD or other autoimmune syndrome.

15. The method of claim 13, comprising administering to the subject identified as having lung damage a therapy to treat the lung damage.

16. A method for determining in a sample the level of IgM antibodies against the peptide consisting of SEQ ID NO: 4, the method comprising contacting the sample with the kit of claim 1.

17. A method for determining in a sample the level of IgM antibodies against the peptide consisting of SEQ ID NO: 4, the method comprising contacting the sample with the kit of claim 6.

18. A method for determining in a sample the level of IgM antibodies against the peptides consisting of SEQ ID NOs: 4, 9, 12, and 15, the method comprising contacting the sample with the kit of claim 2.

19. A method for determining in a sample the level of IgM antibodies against the peptides consisting of SEQ ID NOs: 4, 9, 12, and 15, the method comprising contacting the sample with the kit of claim 6.

* * * * *

SEQUENCE LISTING

<160> NUMBER OF SEQ ID NOS: 17

<210> SEQ ID NO 1
<211> LENGTH: 11
<212> TYPE: PRT
<213> ORGANISM: Artificial

```
<220> FEATURE:
<223> OTHER INFORMATION: amino acid sequence of positions 1-11 of human
      U1Ap

<400> SEQUENCE: 1

Met Ala Val Pro Glu Thr Arg Pro Asn His Thr
1               5                   10

<210> SEQ ID NO 2
<211> LENGTH: 24
<212> TYPE: PRT
<213> ORGANISM: Artificial
<220> FEATURE:
<223> OTHER INFORMATION: amino acid sequence of positions 35-58 of human
      U1Ap

<400> SEQUENCE: 2

Ser Gln Phe Gly Gln Ile Leu Asp Ile Leu Val Ser Arg Ser Leu Lys
1               5                   10                  15

Met Arg Gly Gln Ala Phe Val Ile
            20

<210> SEQ ID NO 3
<211> LENGTH: 13
<212> TYPE: PRT
<213> ORGANISM: Artificial
<220> FEATURE:
<223> OTHER INFORMATION: amino acid sequence of positions 47-59 of human
      U1Ap

<400> SEQUENCE: 3

Arg Ser Leu Lys Met Arg Gly Gln Ala Phe Val Ile Phe
1               5                   10

<210> SEQ ID NO 4
<211> LENGTH: 36
<212> TYPE: PRT
<213> ORGANISM: Artificial
<220> FEATURE:
<223> OTHER INFORMATION: amino acid sequence of positions 60-95 of human
      U1Ap

<400> SEQUENCE: 4

Lys Glu Val Ser Ser Ala Thr Asn Ala Leu Arg Ser Met Gln Gly Phe
1               5                   10                  15

Pro Phe Tyr Asp Lys Pro Met Arg Ile Gln Tyr Ala Lys Thr Asp Ser
            20                  25                  30

Asp Ile Ile Ala
            35

<210> SEQ ID NO 5
<211> LENGTH: 8
<212> TYPE: PRT
<213> ORGANISM: Artificial
<220> FEATURE:
<223> OTHER INFORMATION: amino acid sequence of positions 96-103 of
      human U1Ap

<400> SEQUENCE: 5

Lys Met Lys Gly Thr Phe Val Glu
1               5

<210> SEQ ID NO 6
<211> LENGTH: 8
<212> TYPE: PRT
<213> ORGANISM: Artificial
```

```
<220> FEATURE:
<223> OTHER INFORMATION: amino acid sequence of positions 112-119 of
      human U1Ap

<400> SEQUENCE: 6

Lys Pro Lys Ser Gln Glu Thr Pro
1               5

<210> SEQ ID NO 7
<211> LENGTH: 10
<212> TYPE: PRT
<213> ORGANISM: Artificial
<220> FEATURE:
<223> OTHER INFORMATION: amino acid sequence of positions 118-127 of
      human U1Ap

<400> SEQUENCE: 7

Thr Pro Ala Thr Lys Lys Ala Val Gln Gly
1               5                   10

<210> SEQ ID NO 8
<211> LENGTH: 12
<212> TYPE: PRT
<213> ORGANISM: Artificial
<220> FEATURE:
<223> OTHER INFORMATION: amino acid sequence of positions 143-154 of
      human U1Ap

<400> SEQUENCE: 8

Gly Met Pro Pro Met Thr Gln Ala Pro Arg Ile Met
1               5                   10

<210> SEQ ID NO 9
<211> LENGTH: 20
<212> TYPE: PRT
<213> ORGANISM: Artificial
<220> FEATURE:
<223> OTHER INFORMATION: amino acid sequence of positions 159-178 of
      human U1Ap

<400> SEQUENCE: 9

Gly Gln Pro Pro Tyr Met Pro Pro Gly Met Ile Pro Pro Gly
1               5                   10                  15

Leu Ala Pro Gly
            20

<210> SEQ ID NO 10
<211> LENGTH: 8
<212> TYPE: PRT
<213> ORGANISM: Artificial
<220> FEATURE:
<223> OTHER INFORMATION: amino acid sequence of positions 165-172 of
      human U1Ap

<400> SEQUENCE: 10

Pro Pro Pro Gly Met Ile Pro Pro
1               5

<210> SEQ ID NO 11
<211> LENGTH: 8
<212> TYPE: PRT
<213> ORGANISM: Artificial
<220> FEATURE:
<223> OTHER INFORMATION: amino acid sequence of positions 178-185 of
      human U1Ap

<400> SEQUENCE: 11
```

```
Gly Gln Ile Pro Pro Gly Ala Met
 1               5
```

<210> SEQ ID NO 12
<211> LENGTH: 14
<212> TYPE: PRT
<213> ORGANISM: Artificial
<220> FEATURE:
<223> OTHER INFORMATION: amino acid sequence of positions 180-193 of
      human U1Ap

<400> SEQUENCE: 12

```
Ile Pro Pro Gly Ala Met Pro Pro Gln Gln Leu Met Pro Gly
 1               5                   10
```

<210> SEQ ID NO 13
<211> LENGTH: 8
<212> TYPE: PRT
<213> ORGANISM: Artificial
<220> FEATURE:
<223> OTHER INFORMATION: amino acid sequence of positions 196-203 of
      human U1Ap

<400> SEQUENCE: 13

```
Pro Pro Ala Gln Pro Leu Ser Glu
 1               5
```

<210> SEQ ID NO 14
<211> LENGTH: 32
<212> TYPE: PRT
<213> ORGANISM: Artificial
<220> FEATURE:
<223> OTHER INFORMATION: amino acid sequence of positions 204-235 of
      human U1Ap

<400> SEQUENCE: 14

```
Asn Pro Pro Asn His Ile Leu Phe Leu Thr Asn Leu Pro Glu Glu Thr
 1               5                   10                  15

Asn Glu Leu Met Leu Ser Met Leu Phe Asn Gln Phe Pro Gly Phe Lys
            20                  25                  30
```

<210> SEQ ID NO 15
<211> LENGTH: 8
<212> TYPE: PRT
<213> ORGANISM: Artificial
<220> FEATURE:
<223> OTHER INFORMATION: amino acid sequence of positions 236-242 of
      human U1Ap

<400> SEQUENCE: 15

```
Glu Val Arg Leu Val Pro Gly Arg
 1               5
```

<210> SEQ ID NO 16
<211> LENGTH: 13
<212> TYPE: PRT
<213> ORGANISM: Artificial
<220> FEATURE:
<223> OTHER INFORMATION: amino acid sequence of positions 239-251 of
      human U1Ap

<400> SEQUENCE: 16

```
Leu Val Pro Gly Arg His Asp Ile Ala Phe Val Glu Phe
 1               5                   10
```

<210> SEQ ID NO 17
<211> LENGTH: 26

```
<212> TYPE: PRT
<213> ORGANISM: Artificial
<220> FEATURE:
<223> OTHER INFORMATION: amino acid sequence of positions 257-282 of
      human U1Ap

<400> SEQUENCE: 17

Ala Gly Ala Ala Arg Asp Ala Leu Gln Gly Phe Lys Ile Thr Gln Asn
1               5                   10                  15

Asn Ala Met Lys Ile Ser Phe Ala Lys Lys
            20                  25
```